(12) United States Patent
Defossa et al.

(10) Patent No.: US 7,402,674 B2
(45) Date of Patent: Jul. 22, 2008

(54) 7-PHENYLAMINO-4-QUINOLONE-3-CARBOXYLIC ACID DERIVATIVES, PROCESS FOR THEIR PREPARATION AND THEIR USE AS MEDICAMENTS

(75) Inventors: Elisabeth Defossa, Idstein (DE); Dieter Kadereit, Offenbach (DE); Sven Ruf, Florsheim (DE); Thomas Klabunde, Frankfurt (DE); Dieter Schmoll, Frankfurt (DE); Andreas Herling, Bad Camberg (DE); Karl-Ulrich Wendt, Frankfurt (DE)

(73) Assignee: Sanofi-Aventis Deutschland GmbH,, Frankfurt (DE)

( * ) Notice: Subject to any disclaimer, the term of this patent is extended or adjusted under 35 U.S.C. 154(b) by 468 days.

(21) Appl. No.: 11/042,023

(22) Filed: Jan. 25, 2005

(65) Prior Publication Data
US 2005/0182085 A1 Aug. 18, 2005

Related U.S. Application Data

(60) Provisional application No. 60/582,719, filed on Jun. 24, 2004.

(30) Foreign Application Priority Data

Jan. 31, 2004 (DE) ........................ 10 2004 004 973
Jul. 10, 2004 (DE) ........................ 10 2004 033 405

(51) Int. Cl.
C07D 471/02 (2006.01)
C07D 215/38 (2006.01)
A61K 31/44 (2006.01)
A61K 31/47 (2006.01)

(52) U.S. Cl. ........................ 546/156; 546/153; 546/123; 514/300; 514/312; 514/313

(58) Field of Classification Search ................. 546/156, 546/157, 123, 153; 514/300, 312, 313
See application file for complete search history.

(56) References Cited

U.S. PATENT DOCUMENTS

| | | | |
|---|---|---|---|
| 6,221,633 B1 | 4/2001 | Ertl et al. |
| 6,221,897 B1 | 4/2001 | Frick et al. |
| 6,245,744 B1 | 6/2001 | Frick et al. |
| 6,342,512 B1 | 1/2002 | Kirsch et al. |
| 6,624,185 B2 | 9/2003 | Glombik et al. |

FOREIGN PATENT DOCUMENTS

| | | |
|---|---|---|
| DE | 10142734 | 3/2003 |
| EP | 0 462 884 A1 | 12/1991 |
| WO | WO 97/26265 | 7/1997 |
| WO | WO 97/41097 | 11/1997 |
| WO | WO 98/08871 | 3/1998 |
| WO | WO 99/03861 | 1/1999 |
| WO | WO 99/15525 | 4/1999 |
| WO | WO 00/40569 | 7/2000 |
| WO | WO 00/63208 | 10/2000 |
| WO | WO 00/66585 | 11/2000 |
| WO | WO 00/71549 | 11/2000 |
| WO | WO 00/78312 | 12/2000 |
| WO | WO 01/09111 A1 | 2/2001 |
| WO | 01/85695 | * 11/2001 |
| WO | WO 01/83451 | 11/2001 |
| WO | WO 01/85695 | 11/2001 |
| WO | WO 01/91752 | 12/2001 |
| WO | WO 02/48113 | 6/2002 |
| WO | WO 03/074532 | 9/2003 |

OTHER PUBLICATIONS

3-Quinolinecarboxylic acid, 1,4-dihydro-4-oxo-6-(phenylamino)- (9CI) (CA index name), Database Registry Chemical Abstracts Service (2004) XP002331734.

3-Quinolinecarboxylic acid, 4-hydroxy-6-(phenylamino)—, ethyl ester, Database Chemcats Chemical Abstacts Service XP002331735 (2004).

Asakawa, A., et al., Cocaine-Amphetamine-Regulated Transcript Influences Energy Metabolism, Anxiety and Gastric Emptying in Mice, Hormone and Metabolic Research, 2001, vol 33(9), pp. 554-558.

Drueckes P et al., Photometric Microtiter Assay of Inorganic Phosphate in the Presence of Acid-Labile Organic Phosphates, Anal. Biochem, 1995, vol. 230(1), pp. 173-177.

Engers H.D. et al., Kinetic Mechanism Of Phosphorylase a. I. Initial Velocity Studies, Journal Of Biochemistry, (1970), vol. 48, pp. 746-754.

(Continued)

*Primary Examiner*—D. Margaret Seaman
(74) *Attorney, Agent, or Firm*—Barbara Kurys

(57) ABSTRACT

7-Phenylamino-4-quinolone-3-carboxylic acid derivatives, process for their preparation and their use as medicaments The invention relates to 7-phenylamino-4-quinolone-3-carboxylic acid derivatives and to the physiologically tolerated salts and physiologically functional derivatives thereof.

The invention relates to compounds of the formula I

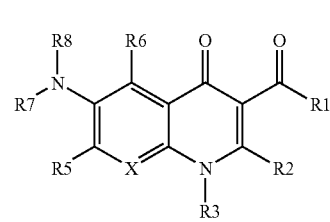

in which the radicals have the stated meanings, and to the physiologically tolerated salts thereof. The compounds are suitable for example as medicaments for the prevention and treatment of type 2 diabetes.

5 Claims, No Drawings

OTHER PUBLICATIONS

Lee Daniel W. et al., Leptin Agonists as a Potential Approach to the Treatment of Obesity, Drugs of the Future, (2001), vol. 26, No. 9, pp. 873-881.

Link, et al., Derivatives of 3-Quinolinecarboxylic Acid with Oxygen Substitution in Position 4,5 and 8: Synthesis, Reactions, NMR.-Studien, Helvectica Chimica Acta (1982) vol. 65, Fasc.8 pp. 2645-2667.

Salvador Javier et al., Perspectives in the Therapeutic Use of Leptin, Expert Opinion Pharmacotherapy, (2001), vol. 2, No. 10, pp. 1615-1622.

Tyle, et. al., Iontophoretic Devices for Drug Delivery, Pharmaceutical Research (1986) vol. 3, No. 6, pp. 318-326.

Wolfe, et. al., Rational Developement of Pratical Catalysts for Aromatic Carbon-Nitrogen Bond Formation, Acc. Chem. Res. (1998) vol. 31 pp. 805-818.

Zunft, H. et al., Carob Pulp Preparation for Treatment of Hypercholesterolemia, Advances in Therapy, 2001, vol. 18(5), pp. 230-236.

* cited by examiner

7-PHENYLAMINO-4-QUINOLONE-3-CARBOXYLIC ACID DERIVATIVES, PROCESS FOR THEIR PREPARATION AND THEIR USE AS MEDICAMENTS

7-Phenylamino-4-quinolone-3-carboxylic acid derivatives, process for their preparation and their use as medicaments The invention relates to 7-phenylamino-4-quinolone-3-carboxylic acid derivatives and to the physiologically tolerated salts and physiologically functional derivatives thereof.

Compounds of similar structure have already been described in the art (Link, Helmut; Bernauer, Karl; Englert Gerhard, Helvetica Chimica Acta 65(8), 1982, 2645-2667 and Bennet et al. J. Chem. Soc., 1949, 227-229).

The invention was based on the object of providing compounds which display a therapeutically usable blood glucose-lowering effect.

The invention therefore relates to compounds of the formula I

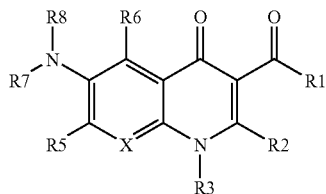

in which the meanings are
R1 OH, O—($C_1$-$C_6$)-alkyl or O—($C_1$-$C_6$)-alkyl-OCO—($C_1$-$C_6$)-alkyl;
R2 H, ($C_1$-$C_6$)-alkyl or phenyl;
R3 H, ($C_1$-$C_8$)-alkyl, ($C_3$-$C_7$)-cycloalkyl, pyridyl or phenyl, where alkyl may be substituted by R9 and where phenyl or pyridyl may be substituted by R10;
R9 $NH_2$, NH—($C_1$-$C_6$)-alkyl, N—(($C_1$-$C_6$)-alkyl)$_2$, COOH, COO—($C_1$-$C_6$)-alkyl, ($C_3$-$C_7$)-cycloalkyl, heteroalkyl, heteroaryl, O-phenyl or phenyl, where phenyl and heteroaryl may be substituted by R11;
R10 F, Cl, Br, ($C_1$-$C_6$-alkyl), O—($C_1$-$C_6$)-alkyl, COOH, COO—($C_1$-$C_6$)-alkyl, $NH_2$, NH—($C_1$-$C_6$)-alkyl or N—(($C_1$-$C_6$)-alkyl)$_2$;
R11 F, Cl, ($C_1$-$C_6$-alkyl), O—($C_1$-$C_6$)-alkyl, $NH_2$, NH—($C_1$-$C_6$)-alkyl, N—(($C_1$-$C_6$)-alkyl)$_2$, COOH or COO—($C_1$-$C_4$)-alkyl;
X C—R4 or N;
R4 H, F, Cl, Br, OH, $NO_2$, CN, ($C_1$-$C_6$)-alkyl or O—($C_1$-$C_6$)-alkyl, where alkyl may be substituted more than once by F, Cl or Br;
R5 H, F, Cl, Br, OH, $NO_2$, CN, ($C_1$-$C_6$)-alkyl or O—($C_1$-$C_6$)-alkyl, where alkyl may be substituted more than once by F, Cl or Br;
R6 H, F, Cl, Br, $NO_2$, CN or ($C_1$-$C_6$)-alkyl, where alkyl may be substituted more than once by F, Cl or Br;
R7 H or ($C_1$-$C_6$)-alkyl;
R8 phenyl, where phenyl may be substituted up to five times by F, Cl, Br, CN, $NO_2$, ($C_1$-$C_8$)-alkyl, O—($C_1$-$C_8$)-alkyl, S—($C_1$-$C_8$)-alkyl, ($C_2$-$C_8$)-alkenyl, ($C_3$-$C_7$)-cycloalkyl, CO—($C_1$-$C_4$)-alkyl, phenyl, benzyl, benzoyl, $NH_2$, NH—($C_1$-$C_6$)-alkyl, N—(($C_1$-$C_6$)-alkyl)$_2$, P(O)—(O—($C_1$-$C_4$)-alkyl)$_2$ or heteroalkyl, where alkyl and alkenyl may be substituted more than once by F, Cl, Br, COOH, or COO—($C_1$-$C_4$)-alkyl;
heteroalkyl heterocyclic, saturated or unsaturated 4- to 7-membered ring which may comprise up to 3 heteroatoms N, O or S as ring members, where the ring may be substituted by F, Cl, Br, CN, $NO_2$, ($C_1$-$C_4$)-alkyl, OH, COOH, COO—($C_1$-$C_4$)-alkyl;

with the exception of compounds of the formula I in which the radicals simultaneously have the following meaning:
X equal to N, R1 equal to OH, R2, R3, R4, R5 and R7 equal to H and R8 equal to unsubstituted phenyl;
and the physiologically tolerated salts thereof.

Preference is given to compounds of the formula I in which one or more radicals have the following meanings:
R1 OH, O—($C_1$-$C_6$)-alkyl or O—($C_1$-$C_6$)-alkyl-OCO—($C_1$-$C_6$)-alkyl;
R2 H, ($C_1$-$C_6$)-alkyl or phenyl;
R3 ($C_1$-$C_8$)-alkyl, ($C_3$-$C_7$)-cycloalkyl, pyridyl or phenyl, where alkyl may be substituted by R9 and where phenyl or pyridyl may be substituted by R10;
R9 $NH_2$, NH—($C_1$-$C_6$)-alkyl, N—(($C_1$-$C_6$)-alkyl)$_2$, COOH, COO—($C_1$-$C_6$)-alkyl, ($C_3$-$C_7$)-cycloalkyl, heteroalkyl, heteroaryl, O-phenyl or phenyl, where phenyl and heteroaryl may be substituted by R11;
R10 F, Cl, Br, ($C_1$-$C_6$-alkyl), O—($C_1$-$C_6$)-alkyl, COOH, COO—($C_1$-$C_6$)-alkyl, $NH_2$, NH—($C_1$-$C_6$)-alkyl or N—(($C_1$-$C_6$)-alkyl)$_2$;
R11 F, Cl, ($C_1$-$C_6$-alkyl), O—($C_1$-$C_6$)-alkyl, $NH_2$, NH—($C_1$-$C_6$)-alkyl, N—(($C_1$-$C_6$)-alkyl)$_2$, COOH or COO—($C_1$-$C_4$)-alkyl;
X C—R4 or N;
R4 H, F, Cl, Br, OH, $NO_2$, CN, ($C_1$-$C_6$)-alkyl or O—($C_1$-$C_6$)-alkyl, where alkyl may be substituted more than once by F, Cl or Br;
R5 H, F, Cl, Br, OH, $NO_2$, CN, ($C_1$-$C_6$)-alkyl or O—($C_1$-$C_6$)-alkyl, where alkyl may be substituted more than once by F, Cl or Br;
R6 H, F, Cl, Br, $NO_2$, CN or ($C_1$-$C_6$)-alkyl, where alkyl may be substituted more than once by F, Cl or Br;
R7 H or ($C_1$-$C_6$)-alkyl;
R8 phenyl, where phenyl may be substituted up to five times by F, Cl, Br, CN, $NO_2$, ($C_1$-$C_8$)-alkyl, O—($C_1$-$C_8$)-alkyl, S—($C_1$-$C_8$)-alkyl, ($C_2$-$C_8$)-alkenyl, ($C_3$-$C_7$)-cycloalkyl, CO—($C_1$-$C_4$)-alkyl, phenyl, benzyl, benzoyl, $NH_2$, NH—($C_1$-$C_6$)-alkyl, N—(($C_1$-$C_6$)-alkyl)$_2$, P(O)—(O—($C_1$-$C_4$)-alkyl)$_2$ or heteroalkyl, where alkyl and alkenyl may be substituted more than once by F, Cl, Br, COOH, or COO—($C_1$-$C_4$)-alkyl;
heteroalkyl heterocyclic, saturated or unsaturated 4- to 7-membered ring which may comprise up to 3 heteroatoms N, O or S as ring members, where the ring may be substituted by F, Cl, Br, CN, $NO_2$, ($C_1$-$C_4$)-alkyl, OH, COOH, COO—($C_1$-$C_4$)-alkyl;

and the physiologically tolerated salts thereof.

Particular preference is given to compounds of the formula I in which one or more radicals have the following meaning:
R1 OH, O—($C_1$-$C_6$)-alkyl or O—($C_1$-$C_6$)-alkyl-OCO—($C_1$-$C_6$)-alkyl;
R2 H;
R3 phenyl, where phenyl may be substituted by R10;
R10 F, Cl, Br, ($C_1$-$C_6$-alkyl), O—($C_1$-$C_6$)-alkyl, COOH, COO—($C_1$-$C_6$)-alkyl, $NH_2$, NH—($C_1$-$C_6$)-alkyl or N—(($C_1$-$C_6$)-alkyl)$_2$;
X C—R4;
R4 H, ($C_1$-$C_6$)-alkyl;
R5 H, F, Cl, ($C_1$-$C_6$)-alkyl;
R6 H;

R7 H;
R8 phenyl, where phenyl may be substituted up to five times by F, Cl;

and the physiologically tolerated salts thereof.

Very particular preference is given to compounds of the formula I in which one or more radicals have the following meaning:
R1 OH, O—($C_1$-$C_6$)-alkyl;
R2 H;
R3 phenyl, where phenyl is substituted by R10;
R10 COOH, COO—($C_1$-$C_6$)-alkyl;
X C—R4;
R4 H, ($C_1$-$C_6$)-alkyl;
R5 F, Cl, ($C_1$-$C_6$)-alkyl;
R6 H;
R7 H;
R8 phenyl, where phenyl is substituted one to five times by F, Cl;

and the physiologically tolerated salts thereof.

Preference is further given to compounds of the formula I in which R8 is phenyl and the latter is substituted twice by F or Cl in ortho and para position or substituted three times by F or Cl in ortho, ortho and para position.

Particular preference is further given to compounds of the formula I in which R8 is phenyl and the latter is substituted three times by F or Cl in ortho, ortho and para position.

The invention relates to compounds of the formula I in the form of their racemates, racemic mixtures and pure enantiomers and to their diastereomers and mixtures thereof.

The alkyl radicals in the substituents R1, R2, R3, R4, R5, R6, R7, R8, R9, R10, R11 and heteroalkyl may be both straight-chain and branched.

If radicals or substituents may occur more than once in the compounds of the formula I, they may all, independently of one another, have the stated meanings and be identical or different.

Pharmaceutically acceptable salts are, because their solubility in water is greater than that of the initial or basic compounds, particularly suitable for medical applications. These salts must have a pharmaceutically acceptable anion or cation. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts are ammonium salts, alkali metal salts (such as sodium and potassium salts), alkaline earth metal salts (such as magnesium and calcium salts), trometamol (2-amino-2-hydroxymethyl-1,3-propanediol), diethanolamine, lysine, or ethylenediamine.

Salts with a pharmaceutically unacceptable anion such as, for example, trifluoroacetate likewise belong within the framework of the invention as useful intermediates for the preparation or purification of pharmaceutically acceptable salts and/or for use in nontherapeutic, for example in vitro, applications.

As used herein, the following definitions will apply unless otherwise stated:

"Patient" means a warm blooded animal, such as for example rat, mice, dogs, cats, guinea pigs, and primates such as humans.

"Treat" or "treating" means to alleviate symptoms, eliminate the causation of the symptoms either on a temporary or permanent basis, or to prevent or slow the appearance of symptoms of the named disorder or condition.

"Therapeutically effective amount" means a quantity of the compound which is effective in treating the named disorder or condition.

"Pharmaceutically acceptable carrier" is a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

The citation of any reference herein should not be construed as an admission that such reference is available as "Prior Art" to the instant application.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference in their entireties.

The term "physiologically functional derivative" used herein refers to any physiologically tolerated derivative of a compound of the formula I of the invention, for example an ester, which on administration to a mammal such as, for example, a human is able to form (directly or indirectly) a compound of the formula I or an active metabolite thereof.

Physiologically functional derivatives include prodrugs of the compounds of the invention. Such prodrugs can be metabolized in vivo to a compound of the invention. These prodrugs may themselves be active or not.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of formula I" hereinafter refer to compound(s) of the formula I as described above, and their salts, solvates and physiologically functional derivatives as described herein.

A heteroaryl radical means a pyridinyl, pyrrolyl, pyrimidinyl, pyrazinyl, indolyl, benzimidazolyl, imidazolyl, pyrazolyl, thiazolyl, thiophenyl or a furanyl radical.

The compound(s) of the formula (I) can also be administered in combination with further active ingredient.

The amount of a compound of formula I necessary to achieve the desired biological effect depends on a number of factors, for example the specific compound chosen, the intended use, the mode of administration and the clinical condition of the patient. The daily dose is generally in the range from 0.3 mg to 100 mg (typically from 3 mg and 50 mg) per day and per kilogram of bodyweight, for example 3-10 mg/kg/day. An intravenous dose may be, for example, in the range from 0.3 mg to 1.0 mg/kg, which can suitably be administered as infusion of 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Thus, ampoules for injections may contain, for example, from 1 mg to 100 mg, and single-dose formulations which can be administered orally, such as, for example, tablets or capsules, may contain, for example, from 1.0 to 1000 mg, typically from 10 to 600 mg. For the therapy of the abovementioned conditions, the compounds of formula I may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be in the form of separate units such as, for example, capsules, cachets, suckable tablets or tablets, each of which contain a defined amount of the compound of formula (I); as powders or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one or more surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise suckable tablets which contain a compound of formula I with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound.

Pharmaceutical compositions suitable for rectal administration are preferably in the form of single-dose suppositories. These can be produced by mixing a compound of the formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single plasters which are suitable for long-term close contact with the patient's epidermis. Such plasters suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 318 (1986).

Further active ingredients suitable for combination products are: all antidiabetics mentioned in the Rote Liste 2003, chapter 12. They may be combined with the compounds of the formula I of the invention in particular for a synergistic improvement of the effect. Administration of the active ingredient combination may take place either by separate administration of the active ingredients to the patient or in the form of combination products in which a plurality of active ingredients are present in one pharmaceutical preparation. Most of the active ingredients listed below are disclosed in the USP Dictionary of USAN and International Drug Names, US Pharmacopeia, Rockville 2001.

Antidiabetics include insulin and insulin derivatives such as, for example, Lantus® (see www.lantus.com) or HMR 1964, fast-acting insulins (see U.S. Pat. No. 6,221,633), GLP-1 derivatives such as, for example, those disclosed in WO 98/08871 of Novo Nordisk A/S, and orally effective hypoglycemic active ingredients.

The orally effective hypoglycemic active ingredients include, preferably, sulfonylureas, biguanidines, meglitinides, oxadiazolidinediones, thiazolidinediones, glucosidase inhibitors, glucagon antagonists, GLP-1 agonists, potassium channel openers such as, for example, those disclosed in WO 97/26265 and WO 99/03861 of Novo Nordisk A/S, insulin sensitizers, inhibitors of liver enzymes involved in the stimulation of gluconeogenesis and/or glycogenolysis, modulators of glucose uptake, compounds which alter lipid metabolism, such as antihyperlipidemic active ingredients and antilipidemic active ingredients, compounds which reduce food intake, PPAR and PXR agonists and active ingredients which act on the ATP-dependent potassium channel of the beta cells.

In one embodiment of the invention, the compounds of the formula I are administered in combination with an HMGCoA reductase inhibitor such as simvastatin, fluvastatin, pravastatin, lovastatin, atorvastatin, cerivastatin, rosuvastatin.

In one embodiment of the invention, the compounds of the formula I are administered in combination with a cholesterol absorption inhibitor such as, for example, ezetimibe, tiqueside, pamaqueside.

In one embodiment of the invention, the compounds of the formula I are administered in combination with a PPAR gamma agonist, such as, for example, rosiglitazone, pioglitazone, JTT-501, GI 262570.

In one embodiment of the invention, the compounds of the formula I are administered in combination with PPAR alpha agonist, such as, for example, GW 9578, GW 7647.

In one embodiment of the invention, the compounds of the formula I are administered in combination with a mixed PPAR alpha/gamma agonist, such as, for example, GW 1536, AVE 8042, AVE 8134, AVE 0847, or as described in PCT/US 11833, PCT/US 11490, DE10142734.4.

In one embodiment of the invention, the compounds of the formula I are administered in combination with a fibrate such as, for example, fenofibrate, clofibrate, bezafibrate.

In one embodiment of the invention, the compounds of the formula I are administered in combination with an MTP inhibitor such as, for example, implitapide, BMS-201038, R-103757.

In one embodiment of the invention, the compounds of the formula I are administered in combination with bile acid absorption inhibitor (see, for example, U.S. Pat. No. 6,245,744 or U.S. Pat. No. 6,221,897), such as, for example, HMR 1741.

In one embodiment of the invention, the compounds of the formula I are administered in combination with a CETP inhibitor, such as, for example, JTF-705.

In one embodiment of the invention, the compounds of the formula I are administered in combination with a polymeric bile acid adsorbent such as, for example, cholestyramine, colesevelam.

In one embodiment of the invention, the compounds of the formula I are administered in combination with an LDL receptor inducer (see U.S. Pat. No. 6,342,512), such as, for example, HMR1171, HMR1586.

In one embodiment of the invention, the compounds of the formula I are administered in combination with an ACAT inhibitor, such as, for example, avasimibe.

In one embodiment of the invention, the compounds of the formula I are administered in combination with an antioxidant, such as, for example, OPC-14117.

In one embodiment of the invention, the compounds of the formula I are administered in combination with a lipoprotein lipase inhibitor, such as, for example, NO-1886.

In one embodiment of the invention, the compounds of the formula I are administered in combination with an ATP-citrate lyase inhibitor, such as, for example, SB-204990.

In one embodiment of the invention, the compounds of the formula I are administered in combination with a squalene synthetase inhibitor, such as, for example, BMS-188494.

In one embodiment of the invention, the compounds of the formula I are administered in combination with a lipoprotein (a) antagonist, such as, for example, CI-1027 or nicotinic acid.

In one embodiment of the invention, the compounds of the formula I are administered in combination with a lipase inhibitor, such as, for example, orlistat.

In one embodiment of the invention, the compounds of the formula I are administered in combination with insulin.

In one embodiment, the compounds of the formula I are administered in combination with a sulfonylurea such as, for example, tolbutamide, glibenclamide, glipizide or glimepiride.

In one embodiment, the compounds of the formula I are administered in combination with a biguanide, such as, for example, metformin.

In one further embodiment, the compounds of the formula I are administered in combination with a meglitinide, such as, for example, repaglinide.

In one embodiment, the compounds of the formula I are administered in combination with a thiazolidinedione, such as, for example, troglitazone, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]phenyl] methyl]-2,4-thiazolidinedione.

In one embodiment, the compounds of the formula I are administered in combination with an α-glucosidase inhibitor, such as, for example, miglitol or acarbose.

In one embodiment, the compounds of the formula I are administered in combination with an active ingredient which acts on the ATP-dependent potassium channel of the beta cells, such as, for example, tolbutamide, glibenclamide, glipizide, glimepiride or repaglinide.

In one embodiment, the compounds of the formula I are administered in combination with more than one of the aforementioned compounds, e.g. in combination with a sulfonylurea and metformin, with a sulfonylurea and acarbose, repaglinide and metformin, insulin and a sulfonylurea, insulin and metformin, insulin and troglitazone, insulin and lovastatin, etc.

In a further embodiment, the compounds of the formula I are administered in combination with CART modulators (see "Cocaine-amphetamine-regulated transcript influences energy metabolism, anxiety and gastric emptying in mice" Asakawa, A, et al., M.: Hormone and Metabolic Research (2001), 33(9), 554-558), NPY antagonists, e.g. naphthalene-1-sulfonic acid {4-[(4-aminoquinazolin-2-ylamino)methyl] cyclohexylmethyl}amide; hydrochloride (CGP 71683A)), $MC_4$ agonists (e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxoethyl]-amide; (WO 01/91752)), orexin antagonists (e.g. 1-(2-methylbenzoxazol-6-yl)-3-[1,5]naphthyridin-4-ylurea; hydrochloride (SB-334867-A)), H3 agonists (3-cyclohexyl-1-(4,4-dimethyl-1,4,6,7-tetrahydroimidazo[4,5-c] pyridin-5-yl)propan-1-one oxalic acid salt (WO 00/63208)); TNF agonists, CRF antagonists (e.g. [2-methyl-9-(2,4,6-trimethylphenyl)-9H-1,3,9-triazafluoren-4-yl]dipropylamine (WO 00/66585)), CRF BP antagonists (e.g. urocortin), urocortin agonists, β3 agonists (e.g. 1-(4-chloro-3-methanesulfonylmethylphenyl)-2-[2-(2,3-dimethyl-1H-indol-6-yloxy)-ethyl amino]-ethanol hydrochloride (WO 01/83451)), MSH (melanocyte-stimulating hormone) agonists, CCK-A agonists (e.g. {2-[4-(4-chloro-2,5-dimethoxyphenyl)-5-(2-cyclohexyl-ethyl)thiazol-2-ylcarbamoyl]-5,7-dimethylindol-1-yl}acetic acid trifluoroacetic acid salt (WO 99/15525)), serotonin reuptake inhibitors (e.g. dexfenfluramine), mixed sertoninergic and noradrenergic compounds (e.g. WO 00/71549), 5HT agonists e.g. 1-(3-ethylbenzofuran-7-yl)piperazine oxalic acid salt (WO 01/09111), bombesin agonists, galanin antagonists, growth hormone (e.g. human growth hormone), growth hormone-releasing compounds (6-benzyloxy-1-(2-diisopropylaminoethylcarbamoyl)-3,4-dihydro-1H-isoquinoline-2-carboxylic acid tert-butyl ester (WO 01/85695)), TRH agonists (see, for example, EP 0 462 884), uncoupling protein 2 or 3 modulators, leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881), DA agonists (bromocriptine, Doprexin), lipase/amylase inhibitors (e.g. WO 00/40569), PPAR modulators (e.g. WO 00/78312), RXR modulators or TR-β agonists.

In one embodiment of the invention, the other active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In one embodiment, the other active ingredient is dexamphatamine or amphetamine.

In one embodiment, the other active ingredient is fenfluramine or dexfenfluramine.

In another embodiment, the other active ingredient is sibutramine.

In one embodiment, the other active ingredient is orlistat.

In one embodiment, the other active ingredient is mazindol or phentermine.

In one embodiment, the compounds of the formula I are administered in combination with bulking agents, preferably insoluble bulking agents (see, for example, carob/Caromax® (Zunft H J; et al., Carob pulp preparation for treatment of hypercholesterolemia, ADVANCES IN THERAPY (2001 September-October), 18(5), 230-6.) Caromax is a carob-containing product from Nutrinova, Nutrition Specialties & Food Ingredients GmbH, Industriepark Höchst, 65926 Frankfurt/Main)). Combination with Caromax® is possible in one preparation or by separate administration of compounds of the formula I and Caromax®. Caromax® can in this connection also be administered in the form of food products such as, for example, in bakery products or muesli bars.

It will be appreciated that every suitable combination of the compounds of the invention with one or more of the aforementioned compounds and optionally one or more further pharmacologically active substances will be regarded as falling within the protection conferred via the present invention.

JTT-705

OPC-14117

-continued

SB-204990

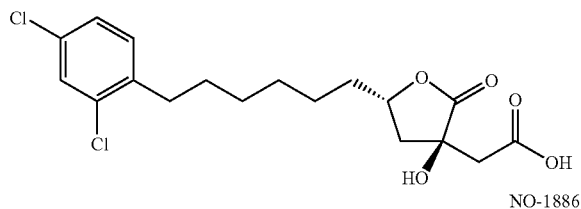

NO-1886

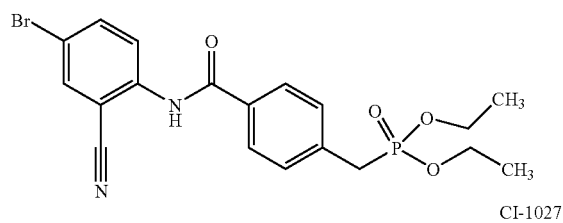

CI-1027

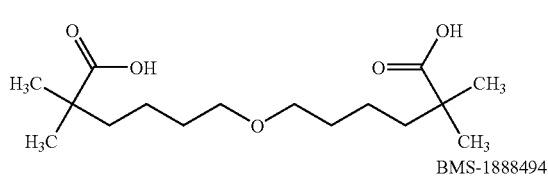

BMS-1888494

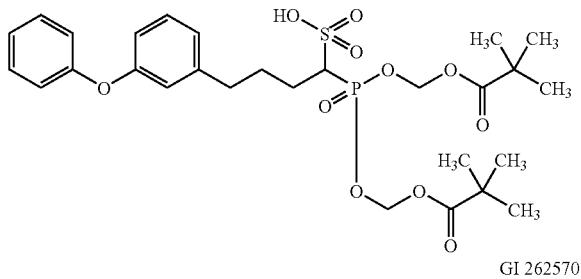

GI 262570

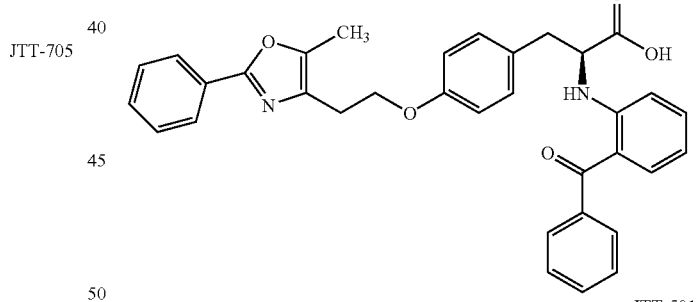

JTT-501

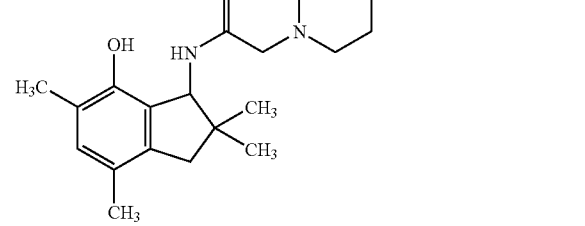

Preparation of the compounds of the formula I is described in the following schemes:

Compounds of the formula II are reacted under Buchwald conditions with amines of the formula III to give compounds of the formula IV in which R1' has the meaning of an ester. In this case, Y is Br, I or triflate. With these Buchwald conditions it is possible to employ catalyst systems with Pd(OAc)$_2$ or Pd$_2$(dba)$_3$ as palladium sources, BINAP, xanthphos and DPPF as ligands and $Cs_2CO_3$, $K_3PO_4$ or $NaO^tBu$ as bases. Solvents which can be used are, for example, toluene, DME, dioxane, THF or DMF. The reaction conditions may be chosen from conventional heating or heating and reaction in a microwave. (Literature: Buchwald, *Acc. Chem. Res.* 1998, 31, 805)

Optional subsequent hydrolysis of the compounds of the formula IV leads to compounds of the formula I.

Scheme 1:

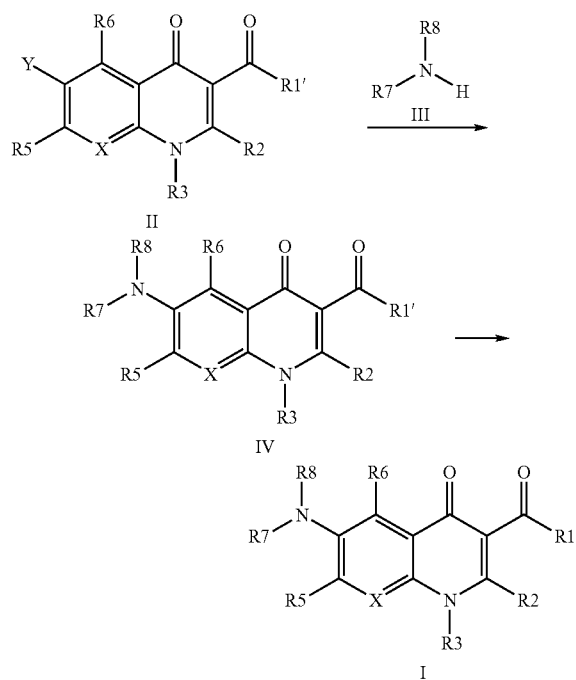

Compounds of the formula II can be prepared by various generally known methods such as, for example, in WO2002 048113. On the one hand, compounds of the general formula II in which X is a carbon atom can be synthesized from the corresponding anilines of the formula V by the Gould Jacobs route, as depicted in scheme 2. The alkylation on nitrogen can be carried out at any point in the synthesis.

Scheme 2:

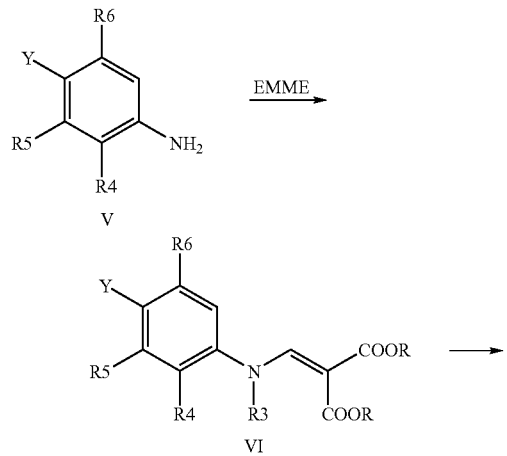

-continued

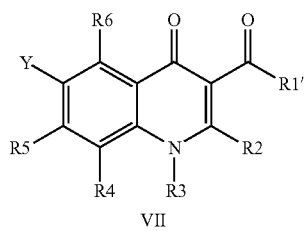

A further aspect of this invention is a novel preparation process for preparing the quinolones of the formula I as shown in scheme 2, wherein the radical Y is an unsubstituted or substituted aniline residue.

On the other hand, compounds of the formula II in which X is a carbon atom can be prepared starting from carboxylic acids of the general formula VIII by conversion into the acid chloride and reaction with malonic ester and orthoformic ester, reaction with amines and subsequent cyclization (scheme 3).

Scheme 3:

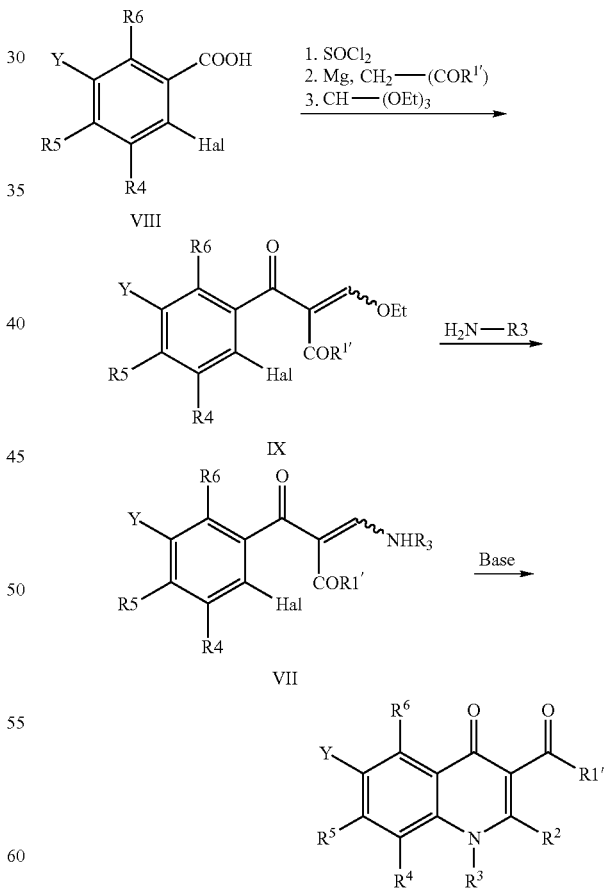

A further aspect of this invention is a novel preparation process for preparing the quinolones of the formula I as shown in scheme 3a, wherein the radical Y is an unsubstituted or substituted aniline residue.

Scheme 3a:

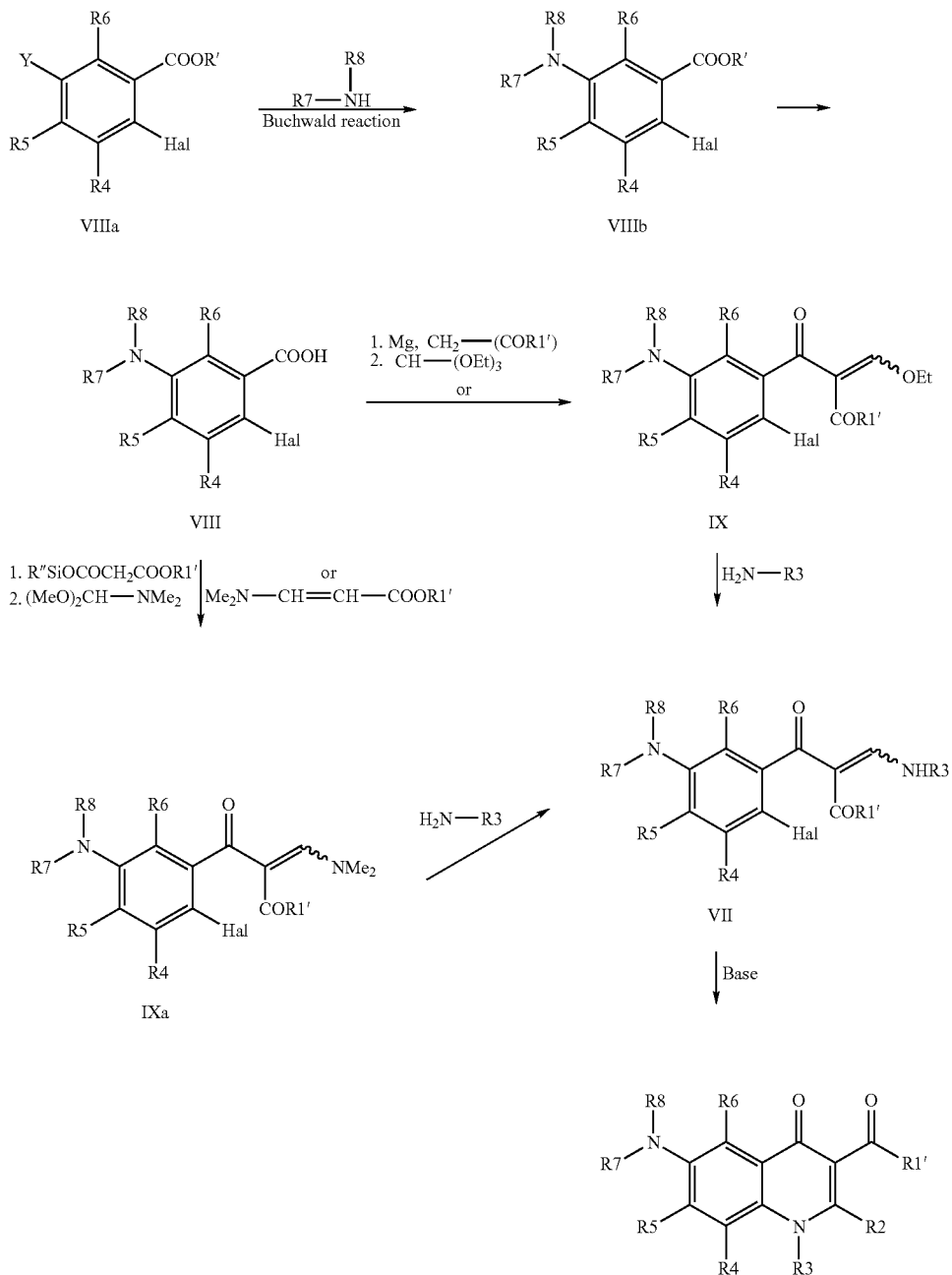

In this preparation method, compounds of the formula VIIIa are reacted under Buchwald conditions (see above) with anilines of the general formula R7R8-NH to give compounds of the general formula VIIIb, where R' is a hydrogen atom or an easily cleavable ester residue. If required, the ester VIIIb is cleaved to give compounds of the formula VIII with choice of suitable conditions. The compounds of the general formula VIII can be converted as described in scheme 3 via the compounds of the formulae IX and VII into compounds of the general formula I. Or else compounds of the general formula VIII are converted into the acid chloride and reacted with 3-dimethylaminoacrylic esters or by reaction with silylmalonic esters and subsequent reaction with dimethyl acetal dimethylformamide to give compounds of the general formula IXa. Compounds of the general formula IXa can be converted by reaction with amines H$_2$N—R3 and subsequent basic ring closure into compounds of the general formula I.

Compounds of the formula II in which X is a nitrogen atom can be prepared in analogy to scheme 4:

Scheme 4:

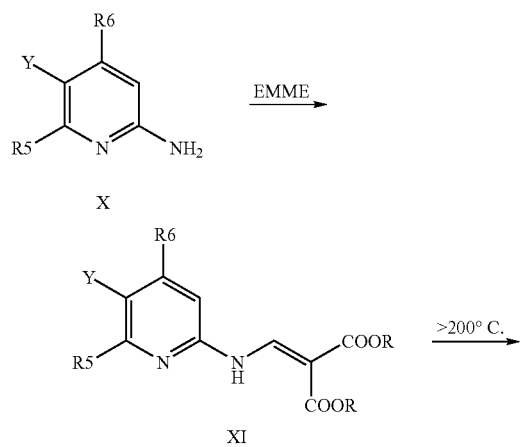

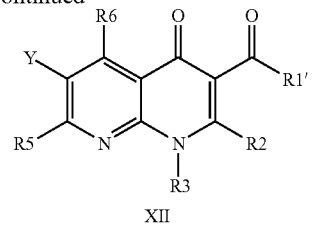

2-Aminopyridines are converted by heating with EMME into compounds of the XI type of structure. These cyclize to give the desired naldic acid derivatives XII at temperatures above 200° C. in a suitable solvent such as DOWTHERM A or diphenyl ether. The cyclization takes place in the form described above only when the substituent R5 is not a hydrogen atom. (Literature: Edmont, Rocher, Plisson, Chenault, *Bioorg. Med. Chem. Lett.* 2000, 1831)

The examples listed below serve to illustrate the invention but without restricting it.

TABLE 1

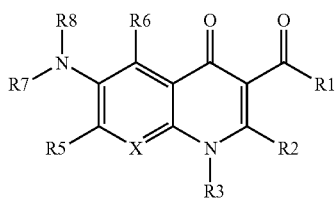

| Example number | R1  | R2 | R3 | X | R5 | R6 | R7 | R8 |
|---|---|---|---|---|---|---|---|---|
| 1 | OEt | H  | Et | N | Me | H  | H  | 4-ethylphenyl |
| 2 | OH  | H  | Et | N | Me | H  | H  | 3-ethylphenyl |
| 3 | OH  | H  | Et | N | Me | H  | H  | 2,4-dimethylphenyl |
| 4 | OEt | H  | Et | N | Me | H  | H  | 2,4-dimethylphenyl |

TABLE 1-continued
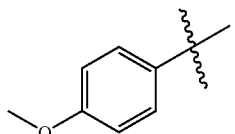
| Example number | R1 | R2 | R3 | X | R5 | R6 | R7 | R8 |
|---|---|---|---|---|---|---|---|---|
| 5 | OEt | H | Et | N | Me | H | H | 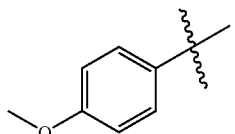 |
| 6 | OEt | H | Et | N | Me | H | H | 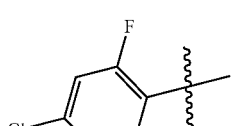 |
| 7 | OEt | H | Et | N | Me | H | H | 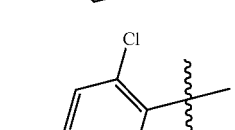 |
| 8 | OEt | H | Et | N | Me | H | H | 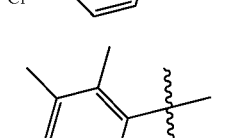 |
| 9 | OEt | H | Et | N | Me | H | H | 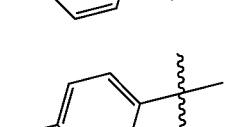 |
| 10 | OEt | H | Et | N | Me | H | H | 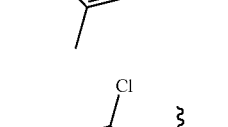 |
| 11 | OEt | H | Et | N | Me | H | H | 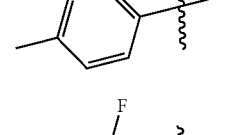 |
| 12 | OEt | H | Et | N | Me | H | H | 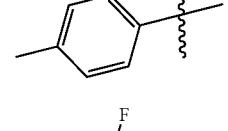 |
| 13 | OEt | H | Et | N | Me | H | H | |

TABLE 1-continued
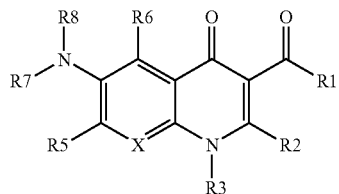
| Example number | R1 | R2 | R3 | X | R5 | R6 | R7 | R8 |
|---|---|---|---|---|---|---|---|---|
| 14 | OEt | H | Et | N | Me | H | H | 3-fluorophenyl |
| 15 | OEt | H | Et | N | Me | H | H | 4-chloro-2-methylphenyl |
| 16 | OEt | H | Et | N | Me | H | H | 3,5-dimethylphenyl |
| 17 | OEt | H | Et | N | Me | H | H | 3-fluoro-5-(trifluoromethyl)phenyl |
| 18 | OH | H | Et | N | Me | H | H | 4-methoxyphenyl |
| 19 | OH | H | Et | N | Me | H | H | 2,4-dichlorophenyl |
| 20 | OH | H | Et | N | Me | H | H | 2,3-dimethylphenyl |
| 21 | OH | H | Et | N | Me | H | H | 2,4-dimethylphenyl |

TABLE 1-continued
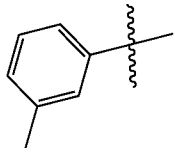
| Example number | R1 | R2 | R3 | X | R5 | R6 | R7 | R8 |
|---|---|---|---|---|---|---|---|---|
| 22 | OH | H | Et | N | Me | H | H | 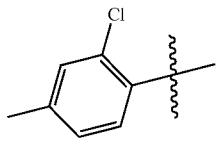 |
| 23 | OH | H | Et | N | Me | H | H | 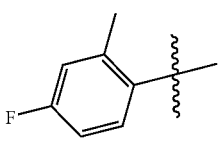 |
| 24 | OH | H | Et | N | Me | H | H | 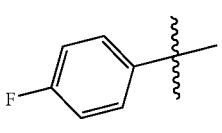 |
| 25 | OH | H | Et | N | Me | H | H | 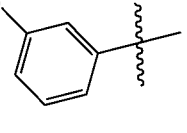 |
| 26 | OH | H | Et | N | Me | H | H | 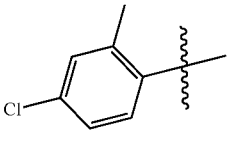 |
| 27 | OH | H | Et | N | Me | H | H | 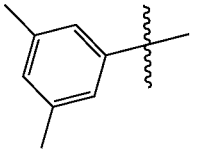 |
| 28 | OH | H | Et | N | Me | H | H | 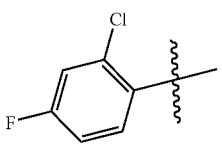 |
| 29 | OH | H | Et | N | Me | H | H | 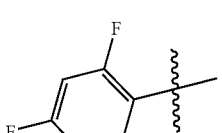 |
| 30 | OH | H | Et | N | Me | H | H |  |

TABLE 1-continued
| Example number | R1 | R2 | R3 | X | R5 | R6 | R7 | R8 |
|---|---|---|---|---|---|---|---|---|
| 31 | OEt | H | Et | N | Me | H | H | 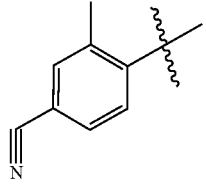 |
| 32 | OEt | H | Et | N | Me | H | H | 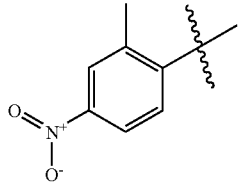 |
| 33 | OH | H | Et | N | Me | H | H | 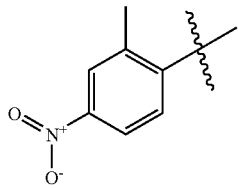 |
| 34 | OH | H | Et | N | Me | H | H | 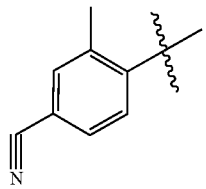 |
| 35 | OEt | H | Et | N | Me | H | H | 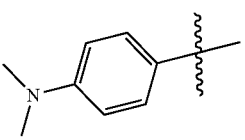 |
| 36 | OEt | H | Et | N | Me | H | H | 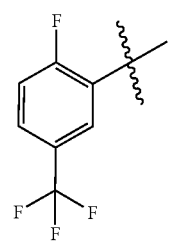 |
| 37 | OEt | H | Et | N | Me | H | H | 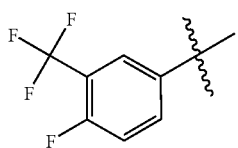 |

TABLE 1-continued
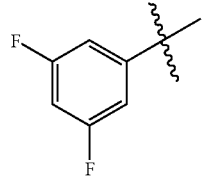
| Example number | R1 | R2 | R3 | X | R5 | R6 | R7 | R8 |
|---|---|---|---|---|---|---|---|---|
| 38 | OEt | H | Et | N | Me | H | H | 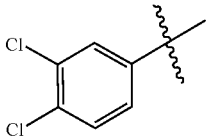 |
| 39 | OEt | H | Et | N | Me | H | H | 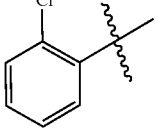 |
| 40 | OEt | H | Et | N | Me | H | H | 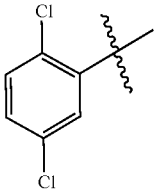 |
| 41 | OEt | H | Et | N | Me | H | H | 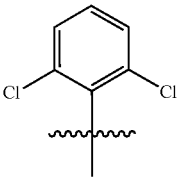 |
| 42 | OEt | H | Et | N | Me | H | H | 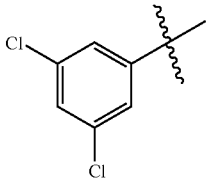 |
| 43 | OEt | H | Et | N | Me | H | H | 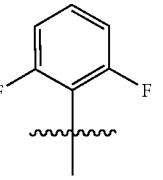 |
| 44 | OEt | H | Et | N | Me | H | H |  |

TABLE 1-continued
| Example number | R1 | R2 | R3 | X | R5 | R6 | R7 | R8 |
|---|---|---|---|---|---|---|---|---|
| 45 | OEt | H | Et | N | Me | H | H | 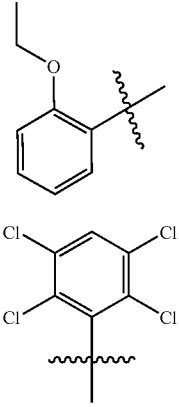 |
| 46 | OEt | H | Et | N | Me | H | H | 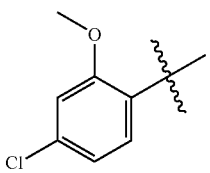 |
| 47 | OEt | H | Et | N | Me | H | H | 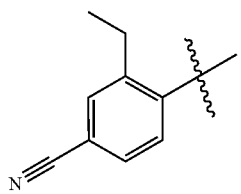 |
| 48 | OEt | H | Et | N | Me | H | H | 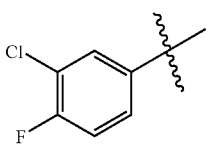 |
| 49 | OEt | H | Et | N | Me | H | H | 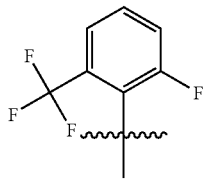 |
| 50 | OEt | H | Et | N | Me | H | H | 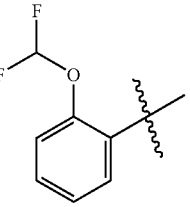 |
| 51 | OEt | H | Et | N | Me | H | H |  |

TABLE 1-continued

| Example number | R1 | R2 | R3 | X | R5 | R6 | R7 | R8 |
| --- | --- | --- | --- | --- | --- | --- | --- | --- |
| 52 | OEt | H | Et | N | Me | H | H | 2,3,5,6-tetrafluorophenyl |
| 53 | OEt | H | Et | N | Me | H | H | 4-(difluoromethoxy)phenyl |
| 54 | OEt | H | Et | N | Me | H | H | 2-fluoro-5-chlorophenyl |
| 55 | OEt | H | Et | N | Me | H | H | 2,3,5-trifluorophenyl |
| 56 | OEt | H | Et | N | Me | H | H | 2-chloro-5-fluorophenyl |
| 57 | OEt | H | Et | N | Me | H | H | 2,4,5-trifluorophenyl |

TABLE 1-continued

| Example number | R1 | R2 | R3 | X | R5 | R6 | R7 | R8 |
|---|---|---|---|---|---|---|---|---|
| 58 | OEt | H | Et | N | Me | H | H | 2-bromo-6-fluorophenyl (CH) |
| 59 | OEt | H | Et | N | Me | H | H | 3-chloro-2-fluorophenyl (CH) |
| 60 | OEt | H | Et | N | Me | H | H | 4-chloro-3-fluorophenyl |
| 61 | OEt | H | Et | N | Me | H | H | 3-fluoro-4-cyanophenyl |
| 62 | OH | H | Et | N | Me | H | H | 3,5-difluorophenyl |
| 63 | OH | H | Et | N | Me | H | H | 2,5-difluorophenyl |
| 64 | OH | H | Et | N | Me | H | H | 2-chlorophenyl |

TABLE 1-continued

| Example number | R1 | R2 | R3 | X | R5 | R6 | R7 | R8 |
|---|---|---|---|---|---|---|---|---|
| 65 | OH | H | Et | N | Me | H | H | 2,3-dichlorophenyl |
| 66 | OH | H | Et | N | Me | H | H | 2,5-dichlorophenyl |
| 67 | OH | H | Et | N | Me | H | H | 2,6-dichlorophenyl |
| 68 | OH | H | Et | N | Me | H | H | 2-ethoxyphenyl |
| 69 | OH | H | Et | N | Me | H | H | 5-chloro-2-methoxyphenyl |
| 70 | OH | H | Et | N | Me | H | H | 4-cyano-2-ethylphenyl |

TABLE 1-continued
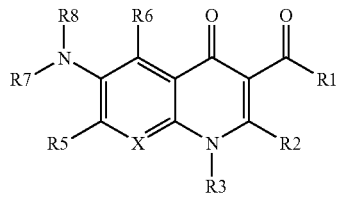
| Example number | R1 | R2 | R3 | X | R5 | R6 | R7 | R8 |
|---|---|---|---|---|---|---|---|---|
| 71 | OH | H | Et | N | Me | H | H | 4-(SCF₃)-phenyl |
| 72 | OH | H | Et | N | Me | H | H | 3-Cl-4-F-phenyl |
| 73 | OH | H | Et | N | Me | H | H | 2-(OCHF₂)-phenyl |
| 74 | OH | H | Et | N | Me | H | H | 2-Cl-6-F-phenyl |
| 75 | OH | H | Et | N | Me | H | H | 2,4,6-trifluorophenyl |
| 76 | OH | H | Et | N | Me | H | H | 2,3,5-trifluorophenyl |

TABLE 1-continued
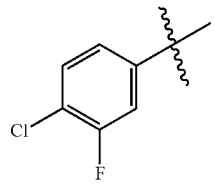
| Example number | R1 | R2 | R3 | X | R5 | R6 | R7 | R8 |
|---|---|---|---|---|---|---|---|---|
| 77 | OH | H | Et | N | Me | H | H | 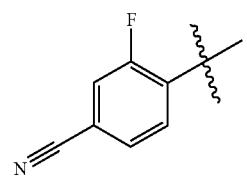 |
| 78 | OH | H | Et | N | Me | H | H | 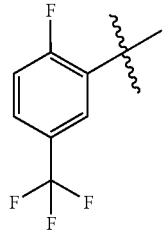 |
| 79 | OH | H | Et | N | Me | H | H | 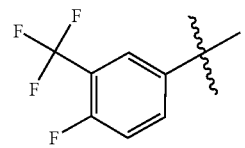 |
| 80 | OH | H | Et | N | Me | H | H | 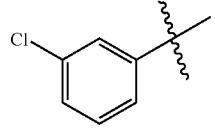 |
| 81 | OH | H | Et | N | Me | H | H | 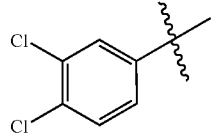 |
| 82 | OH | H | Et | N | Me | H | H | 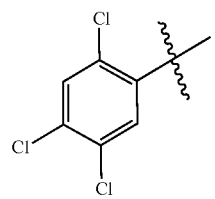 |
| 83 | OH | H | Et | N | Me | H | H |  |

TABLE 1-continued
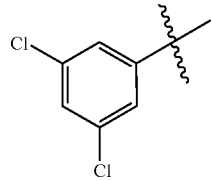
| Example number | R1 | R2 | R3 | X | R5 | R6 | R7 | R8 |
|---|---|---|---|---|---|---|---|---|
| 84 | OH | H | Et | N | Me | H | H | 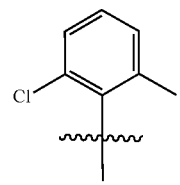 |
| 85 | OH | H | Et | N | Me | H | H | 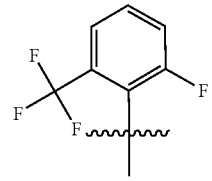 |
| 86 | OH | H | Et | N | Me | H | H | 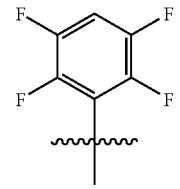 |
| 87 | OH | H | Et | N | Me | H | H | 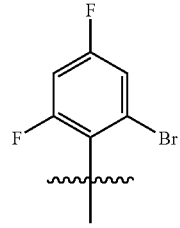 |
| 88 | OH | H | Et | N | Me | H | H | 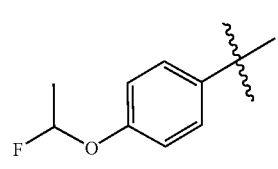 |
| 89 | OH | H | Et | N | Me | H | H |  |

TABLE 1-continued
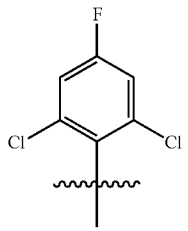
| Example number | R1 | R2 | R3 | X | R5 | R6 | R7 | R8 |
|---|---|---|---|---|---|---|---|---|
| 90 | OH | H | Et | N | Me | H | H | 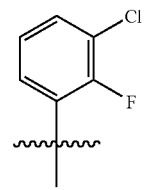 |
| 91 | OH | H | Et | N | Me | H | H | 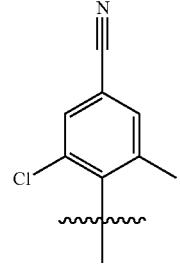 |
| 92 | OH | H | Et | N | Me | H | H | 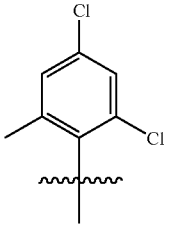 |
| 93 | OH | H | Et | N | Me | H | H | 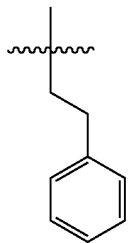 |
| 94 | OEt | H | 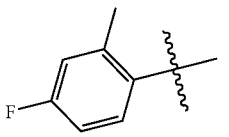 | N | Me | H | H |  |

TABLE 1-continued

| Example number | R1 | R2 | R3 | X | R5 | R6 | R7 | R8 |
|---|---|---|---|---|---|---|---|---|
| 95 | OEt | H | -CH2CH2-N(Me)2 | N | Me | H | H | 4-F, 2-Me-phenyl |
| 96 | OH | H | -CH2CH2-phenyl | N | Me | H | H | 2-Me, 4-F-phenyl |
| 97 | OEt | H | -CH2CH2-N(Me)2 | N | Me | H | H | 2-Cl-phenyl |
| 98 | OH | H | 2-Cl-phenyl-CH2- | N | Me | H | H | 2-Cl-phenyl |
| 99 | OH | H | -CH2CH2-N(Me)2 | N | Me | H | H | 2-Me, 4-F-phenyl |

TABLE 1-continued
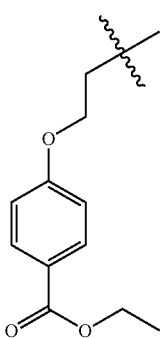
| Example number | R1 | R2 | R3 | X | R5 | R6 | R7 | R8 |
|---|---|---|---|---|---|---|---|---|
| 100 | OEt | H | 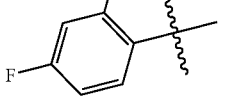 | N | Me | H | H | 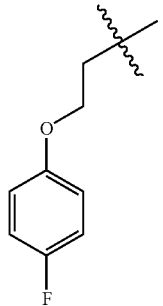 |
| 101 | OEt | H | 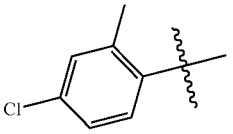 | N | Me | H | H | 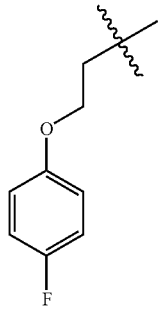 |
| 102 | OEt | H | 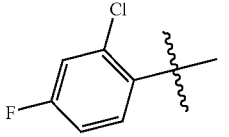 | N | Me | H | H | 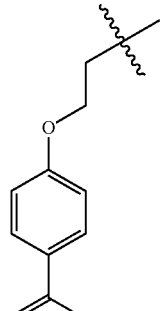 |
| 103 | OH | H | 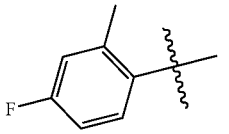 | N | Me | H | H |  |

TABLE 1-continued
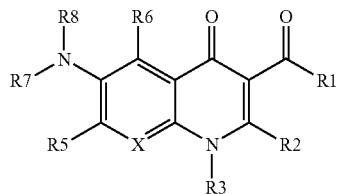
| Example number | R1 | R2 | R3 | X | R5 | R6 | R7 | R8 |
|---|---|---|---|---|---|---|---|---|
| 104 | OH | H | 4-(carboxy)phenoxyethyl | N | Me | H | H | 2-chloro-4-fluorophenyl |
| 105 | OEt | H | 2-(4-fluorophenoxy)ethyl | N | Me | H | H | 4-fluoro-2-methylphenyl |
| 106 | OH | H | 2-(4-fluorophenoxy)ethyl | N | Me | H | H | 2-chloro-4-fluorophenyl |
| 107 | OEt | H | 3-(dimethylamino)propyl | N | Me | H | H | 2-chloro-4,6-difluorophenyl |

TABLE 1-continued
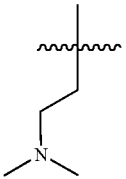
| Example number | R1 | R2 | R3 | X | R5 | R6 | R7 | R8 |
|---|---|---|---|---|---|---|---|---|
| 108 | OH | H | 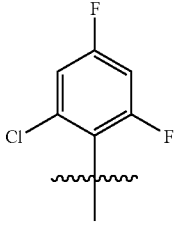 | N | Me | H | H | 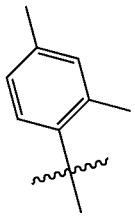 |
| 109 | OH | H | Et | C—Me | H | H | H | 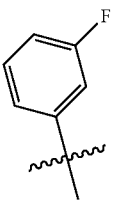 |
| 110 | OH | H | Et | C—Me | H | H | H | 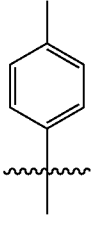 |
| 111 | OH | H | Et | C—Me | H | H | H | 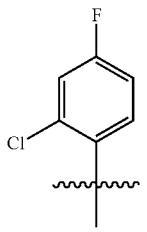 |
| 112 | OMe | H | Et | C—Me | H | H | H |  |

TABLE 1-continued
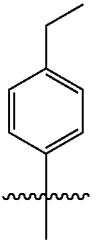
| Example number | R1 | R2 | R3 | X | R5 | R6 | R7 | R8 |
|---|---|---|---|---|---|---|---|---|
| 113 | OMe | H | Et | C—Me | H | H | H | 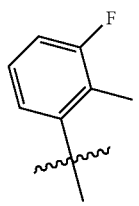 |
| 114 | OMe | H | Et | C—Me | H | H | H | 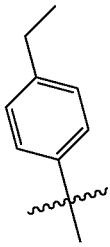 |
| 115 | OH | H | Et | C—Me | H | H | H | 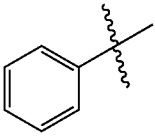 |
| 116 | OH | H | Me | CH | H | H | H | 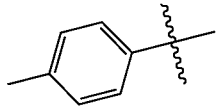 |
| 117 | OMe | H | Me | CH | H | H | H | 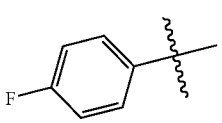 |
| 118 | OMe | H | Me | CH | H | H | H | 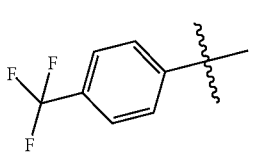 |
| 119 | OMe | H | Me | CH | H | H | H |  |

TABLE 1-continued

| Example number | R1 | R2 | R3 | X | R5 | R6 | R7 | R8 |
|---|---|---|---|---|---|---|---|---|
| 120 | OMe | H | Me | CH | H | H | H | 4-methoxyphenyl |
| 121 | OMe | H | Me | CH | H | H | H | 4-ethylphenyl |
| 122 | OH | H | Et | C—Me | H | H | H | 2,6-dimethylphenyl |
| 123 | OH | H | Et | C—Me | H | H | H | 2,3-dimethylphenyl |
| 124 | OH | H | Et | C—Me | H | H | H | 3,4-dimethylphenyl |
| 125 | OMe | H | Me | CH | H | H | H | 4-bromophenyl |
| 126 | OMe | H | Me | CH | H | H | H | 4-chlorophenyl |
| 127 | OH | H | Me | CH | H | H | H | 4-bromophenyl |

TABLE 1-continued

| Example number | R1 | R2 | R3 | X | R5 | R6 | R7 | R8 |
|---|---|---|---|---|---|---|---|---|
| 128 | OH | H | Me | CH | H | H | H | 4-methoxyphenyl |
| 129 | OH | H | Me | CH | H | H | H | 4-fluorophenyl |
| 130 | OH | H | Me | CH | H | H | H | 4-methylphenyl |
| 131 | OH | H | Me | CH | H | H | H | 4-trifluoromethylphenyl |
| 132 | OH | H | Me | CH | H | H | H | 4-ethylphenyl |
| 133 | OMe | H | Et | C—Me | H | H | H | 2,4,6-trimethylphenyl |
| 134 | OMe | H | Et | C—Me | H | H | H | 4-tert-butyl-3,5-dimethylphenyl |

TABLE 1-continued
| Example number | R1 | R2 | R3 | X | R5 | R6 | R7 | R8 |
|---|---|---|---|---|---|---|---|---|
| 135 | OMe | H | Et | C—Me | H | H | H | 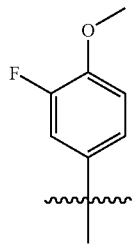 |
| 136 | OH | H | Et | C—Me | H | H | H | 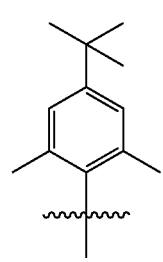 |
| 137 | OMe | H | Et | C—Me | H | H | H | 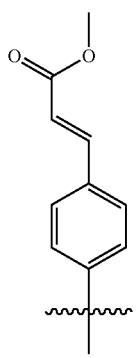 |
| 138 | OH | H | Et | C—Me | H | H | H | 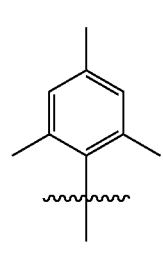 |
| 139 | OMe | H | Et | C—Me | H | H | H | 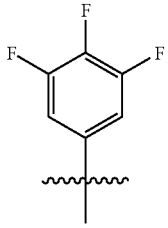 |

TABLE 1-continued
| Example number | R1 | R2 | R3 | X | R5 | R6 | R7 | R8 |
|---|---|---|---|---|---|---|---|---|
| 140 | OMe | H | Et | C—Me | H | H | H | 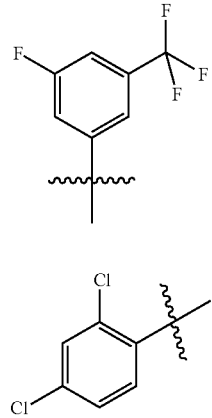 |
| 141 | OMe | H | Me | CH | H | H | H | 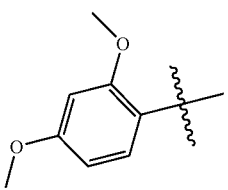 |
| 142 | OMe | H | Me | CH | H | H | H | 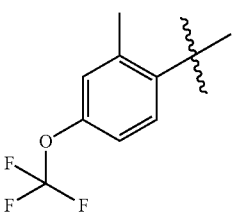 |
| 143 | OMe | H | Me | CH | H | H | H | 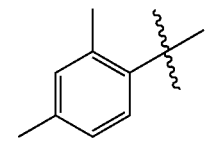 |
| 144 | OMe | H | Me | CH | H | H | H | |
| 145 | OH | H | Me | CH | H | H | H | 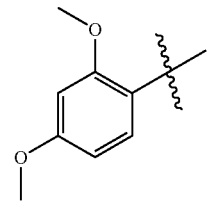 |

TABLE 1-continued
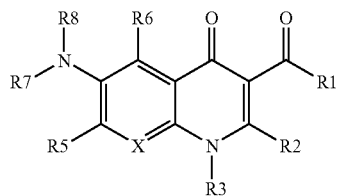
| Example number | R1 | R2 | R3 | X | R5 | R6 | R7 | R8 |
|---|---|---|---|---|---|---|---|---|
| 146 | OH | H | Me | CH | H | H | H | 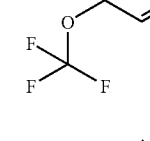 |
| 147 | OH | H | Me | CH | H | H | H | 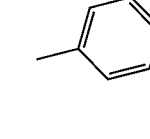 |
| 148 | OH | H | Et | C—Me | H | H | H | 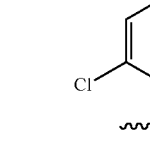 |
| 149 | OH | H | Me | CH | H | H | H | 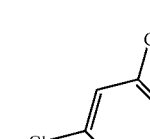 |
| 150 | OH | H | Et | C—Me | H | H | H | 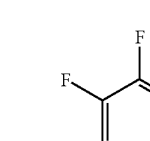 |
| 151 | OMe | H | Et | C—Me | H | H | H | 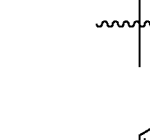 |

TABLE 1-continued
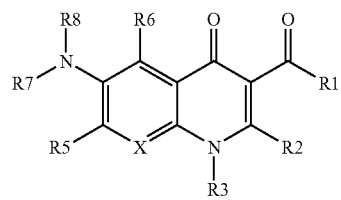
| Example number | R1 | R2 | R3 | X | R5 | R6 | R7 | R8 |
|---|---|---|---|---|---|---|---|---|
| 152 | OMe | H | Et | C—Me | H | H | H | 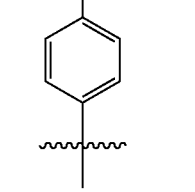 |
| 153 | OMe | H | Et | C—Me | H | H | H | 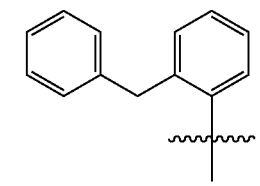 |
| 154 | OMe | H | Et | C—Me | H | H | H | 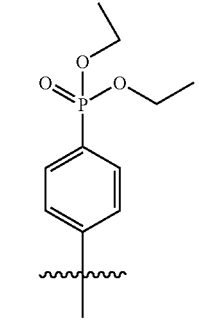 |
| 155 | OMe | H | Et | C—Me | H | H | H | 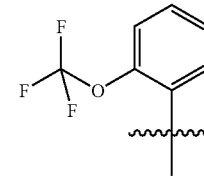 |
| 156 | OMe | H | Et | C—Me | H | H | H | 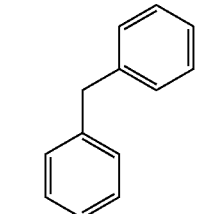 |

TABLE 1-continued
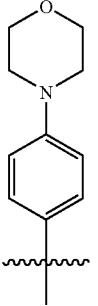
| Example number | R1 | R2 | R3 | X | R5 | R6 | R7 | R8 |
|---|---|---|---|---|---|---|---|---|
| 157 | OMe | H | Et | C—Me | H | H | H | 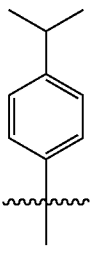 |
| 158 | OMe | H | Et | C—Me | H | H | H | 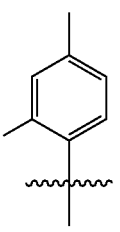 |
| 159 | OMe | H | Et | C—Me | H | H | H | 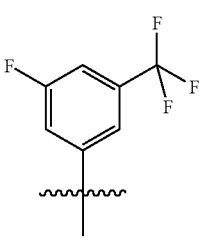 |
| 160 | OH | H | Et | C—Me | H | H | H | 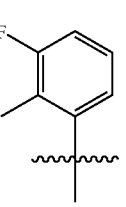 |
| 161 | OH | H | Et | C—Me | H | H | H |  |

TABLE 1-continued
| Example number | R1 | R2 | R3 | X | R5 | R6 | R7 | R8 |
|---|---|---|---|---|---|---|---|---|
| 162 | OH | H | Et | C—Me | H | H | H | 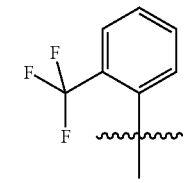 |
| 163 | OH | H | Et | C—Me | H | H | H | 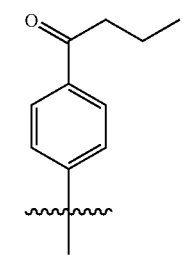 |
| 164 | OH | H | Et | C—Me | H | H | H | 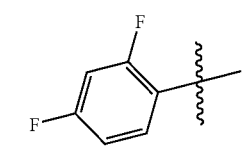 |
| 165 | OMe | H | Me | CH | H | H | H | 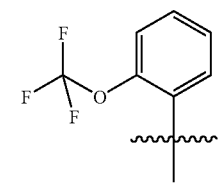 |
| 166 | OH | H | Et | C—Me | H | H | H | 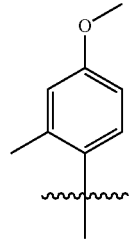 |
| 167 | OMe | H | Et | C—Me | H | H | H |  |

TABLE 1-continued

| Example number | R1 | R2 | R3 | X | R5 | R6 | R7 | R8 |
|---|---|---|---|---|---|---|---|---|
| 168 | OMe | H | Et | C—Me | H | H | H | 4-chloro-2-methylphenyl |
| 169 | OMe | H | Et | C—Me | H | H | H | 2-methyl-4-(trifluoromethoxy)phenyl |
| 170 | OMe | H | Et | C—Me | H | H | H | 4-(ethoxycarbonylmethyl)phenyl |
| 171 | OH | H | Et | C—Me | H | H | H | 2-benzylphenyl |
| 172 | OMe | H | Me | CH | H | H | H | 1-(2-fluoro-4-chlorophenyl)ethyl |

TABLE 1-continued
| Example number | R1 | R2 | R3 | X | R5 | R6 | R7 | R8 |
|---|---|---|---|---|---|---|---|---|
| 173 | OMe | H | Me | CH | H | H | H | 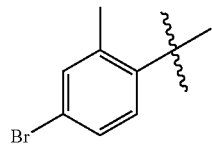 |
| 174 | OMe | H | Me | CH | H | H | H | 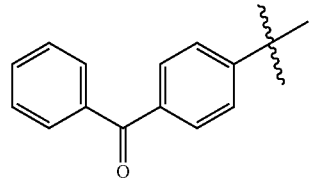 |
| 175 | OMe | H | Me | CH | H | H | H | 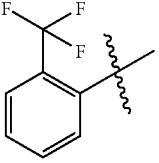 |
| 176 | OMe | H | Et | C—Me | H | H | H | 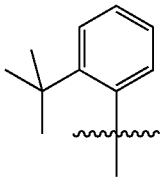 |
| 177 | OEt | H | 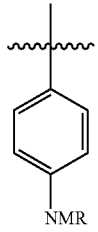 | CH | H | H | H | 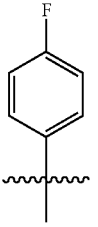 |
| 178 | OMe | H | Et | C—Me | H | H | H | 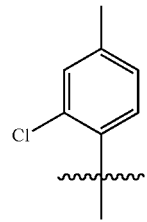 |

TABLE 1-continued
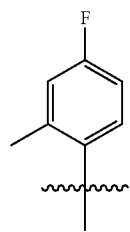
| Example number | R1 | R2 | R3 | X | R5 | R6 | R7 | R8 |
|---|---|---|---|---|---|---|---|---|
| 179 | OH | H | Et | C—Me | H | H | H | 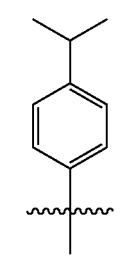 |
| 180 | OH | H | Et | C—Me | H | H | H | 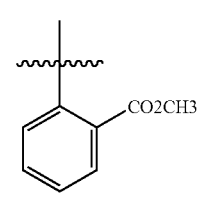 |
| 181 | OEt | H | 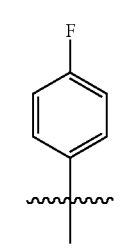 | CH | H | H | H | 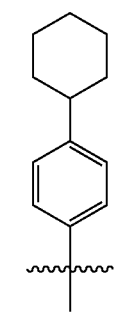 |
| 182 | OMe | H | Et | C—Me | H | H | H | 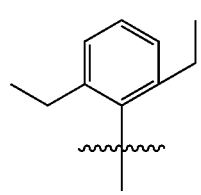 |
| 183 | OMe | H | Et | C—Me | H | H | H |  |

TABLE 1-continued
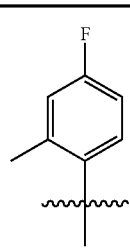
| Example number | R1 | R2 | R3 | X | R5 | R6 | R7 | R8 |
|---|---|---|---|---|---|---|---|---|
| 184 | OMe | H | Et | C—Me | H | H | H | 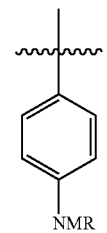 |
| 185 | OEt | H | 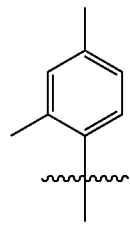 | CH | H | H | H | 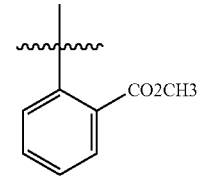 |
| 186 | OEt | H | 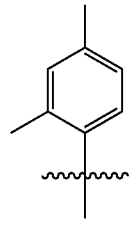 | CH | H | H | H | 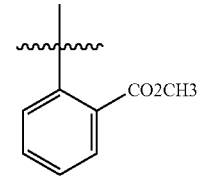 |
| 187 | OH | H | Et | C—Me | H | H | H | 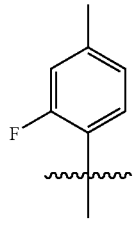 |
| 188 | OH | H | Et | C—Me | H | H | H | 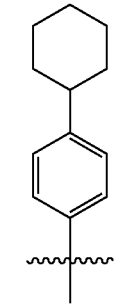 |

TABLE 1-continued

| Example number | R1 | R2 | R3 | X | R5 | R6 | R7 | R8 |
|---|---|---|---|---|---|---|---|---|
| 189 | OH | H | Et | C—Me | H | H | H | 2-Cl-4-Me-phenyl |
| 190 | OH | H | Et | C—Me | H | H | H | 4-Cl-2-Me-phenyl |
| 191 | OH | H | Et | C—Me | H | H | H | 4-OCF₃-2-Me-phenyl |
| 192 | OH | H | Me | CH | H | H | H | 4-isopropyl-phenyl |
| 193 | OH | H | Me | CH | H | H | H | 2,4-difluoro-phenyl |
| 194 | OH | H | Me | CH | H | H | H | 4-Cl-phenyl |

TABLE 1-continued
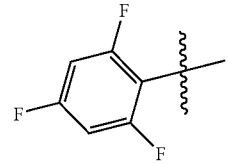
| Example number | R1 | R2 | R3 | X | R5 | R6 | R7 | R8 |
|---|---|---|---|---|---|---|---|---|
| 195 | OH | H | Me | CH | H | H | H | 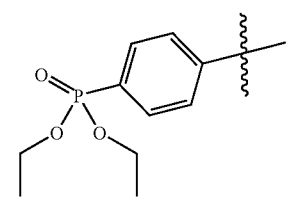 |
| 196 | OH | H | Me | CH | H | H | H | 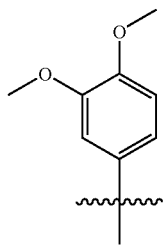 |
| 197 | OMe | H | Et | C—Me | H | H | H | 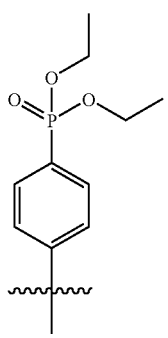 |
| 198 | OH | H | Et | C—Me | H | H | H | 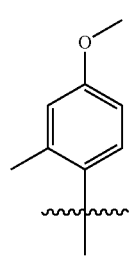 |
| 199 | OH | H | Et | C—Me | H | H | H |  |

TABLE 1-continued

| Example number | R1 | R2 | R3 | X | R5 | R6 | R7 | R8 |
|---|---|---|---|---|---|---|---|---|
| 200 | OEt | H | 3-carboxyphenyl | CH | H | H | H | 4-fluorophenyl |
| 201 | OH | H | 2-carboxyphenyl | CH | H | H | H | 2,4-dimethylphenyl |
| 202 | OH | H | Et | C—Me | H | H | H | 3,4-dimethoxyphenyl |
| 203 | OEt | H | Et | C—Me | H | H | H | 4-fluoro-2-methylphenyl |
| 204 | OEt | H | cyclopropylmethyl | C—Me | H | H | H | 4-fluoro-2-methylphenyl |

TABLE 1-continued
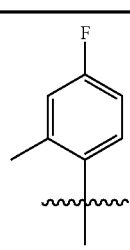
| Example number | R1 | R2 | R3 | X | R5 | R6 | R7 | R8 |
|---|---|---|---|---|---|---|---|---|
| 205 | OH | H | H | C—Me | H | H | H | 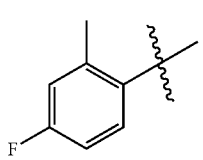 |
| 206 | OMe | H | Et | CH | Cl | H | H | 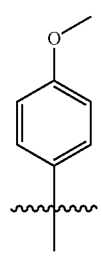 |
| 207 | OMe | H | Et | C—Me | H | H | H | 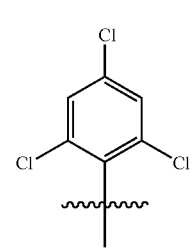 |
| 208 | OMe | H | Et | C—Me | H | H | H | 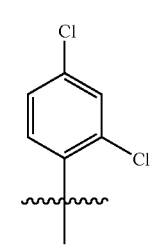 |
| 209 | OMe | H | Et | C—Me | H | H | H | 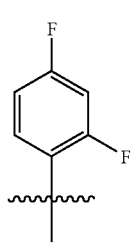 |
| 210 | OMe | H | Et | C—Me | H | H | H |  |

TABLE 1-continued
| Example number | R1 | R2 | R3 | X | R5 | R6 | R7 | R8 |
|---|---|---|---|---|---|---|---|---|
| 211 | OMe | H | Et | C—Me | H | H | H | 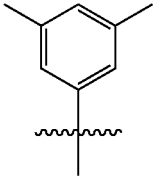 |
| 212 | OEt | H | H | C—Me | H | H | H | 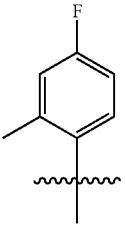 |
| 213 | OH | H | Et | CH | Cl | H | H | 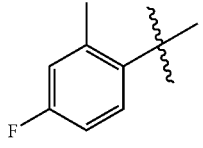 |
| 214 | OMe | H | Et | C—Me | H | H | H | 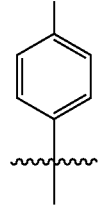 |
| 215 | OH | H | Et | C—Me | H | H | H | 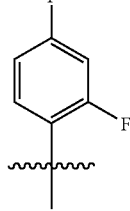 |
| 216 | OH | H | Et | C—Me | H | H | H | 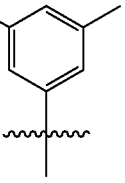 |

TABLE 1-continued
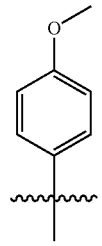
| Example number | R1 | R2 | R3 | X | R5 | R6 | R7 | R8 |
|---|---|---|---|---|---|---|---|---|
| 217 | OH | H | Et | C—Me | H | H | H | 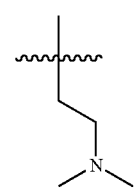 |
| 218 | OEt | H | 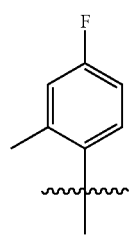 | CH | H | H | H | 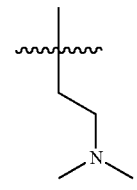 |
| 219 | OH | H | 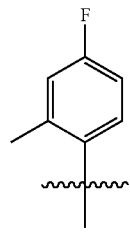 | CH | H | H | H | 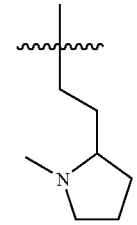 |
| 220 | OEt | H | 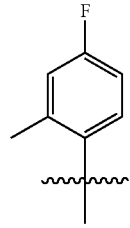 | CH | H | H | H | 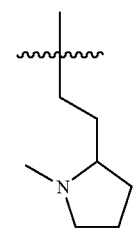 |
| 221 | OH | H | 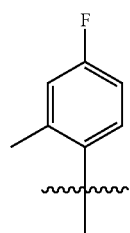 | CH | H | H | H | |

TABLE 1-continued
| Example number | R1 | R2 | R3 | X | R5 | R6 | R7 | R8 |
|---|---|---|---|---|---|---|---|---|
| 222 | OH | H | Et | C—Me | H | H | H | 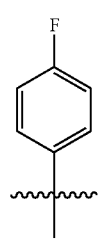 |
| 223 | OMe | H | Et | C—Me | H | H | H | 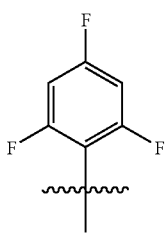 |
| 224 | OEt | H | Et | C—OCF$_3$ | H | H | H | 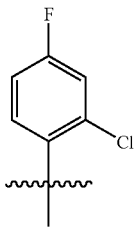 |
| 225 | OEt | H | Et | C—OCF$_3$ | H | H | H | 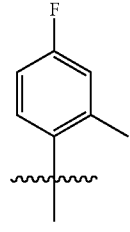 |
| 226 | OMe | H | Me | CH | H | H | H | 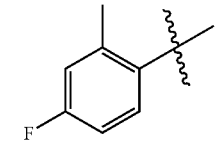 |

TABLE 1-continued
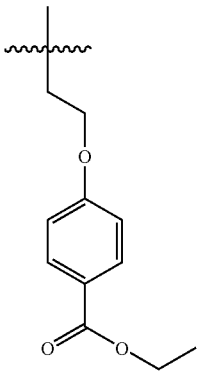
| Example number | R1 | R2 | R3 | X | R5 | R6 | R7 | R8 |
|---|---|---|---|---|---|---|---|---|
| 227 | OEt | H | 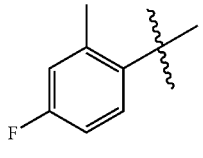 | CH | H | H | H | 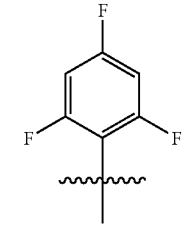 |
| 228 | OH | H | Et | C—Me | H | H | H | 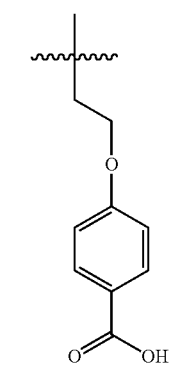 |
| 229 | OH | H | 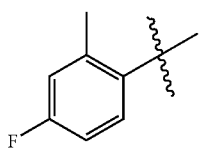 | CH | H | H | H | 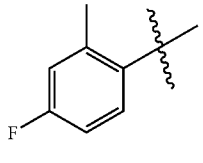 |
| 230 | OH | H | Me | CH | H | H | H |  |

TABLE 1-continued

| Example number | R1 | R2 | R3 | X | R5 | R6 | R7 | R8 |
|---|---|---|---|---|---|---|---|---|
| 231 | OEt | H | Et | CH | F | H | H | 4-F, 2-Cl-phenyl |
| 232 | OH | H | Et | C—OCF₃ | H | H | H | 4-F, 2-Cl-phenyl |
| 233 | OH | H | Et | C—OCF₃ | H | H | H | 4-F, 2-Me-phenyl |
| 234 | OMe | H | Et | C—Me | H | H | H | 4-CN, 2-Me-phenyl |
| 235 | OH | H | CH₂CH₂N(Me)₂ | CH | Cl | H | H | 4-F, 2-Me-phenyl |

TABLE 1-continued
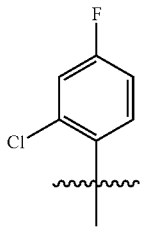
| Example number | R1 | R2 | R3 | X | R5 | R6 | R7 | R8 |
|---|---|---|---|---|---|---|---|---|
| 236 | OH | Me | Et | CH | H | H | H | 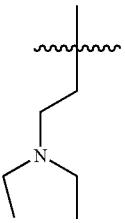 |
| 237 | OEt | H | 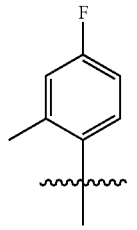 | CH | H | H | H | 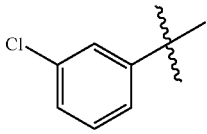 |
| 238 | OMe | H | Et | C—Me | H | H | H | 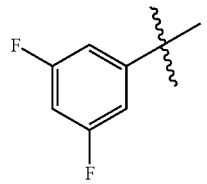 |
| 239 | OMe | H | Et | C—Me | H | H | H | 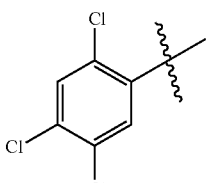 |
| 240 | OMe | H | Et | C—Me | H | H | H | 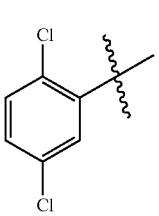 |
| 241 | OMe | H | Et | C—Me | H | H | H |  |

TABLE 1-continued
| Example number | R1 | R2 | R3 | X | R5 | R6 | R7 | R8 |
|---|---|---|---|---|---|---|---|---|
| 242 | OMe | H | Et | C—Me | H | H | H | 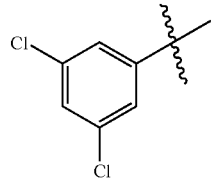 |
| 243 | OMe | H | Et | C—Me | H | H | H | 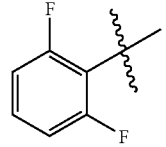 |
| 244 | OMe | H | Et | C—Me | H | H | H | 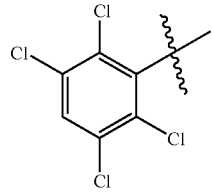 |
| 245 | OMe | H | Et | C—Me | H | H | H | 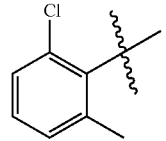 |
| 246 | OMe | H | Et | C—Me | H | H | H | 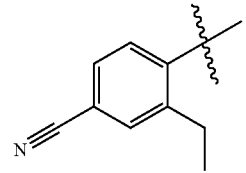 |
| 247 | OMe | H | Et | C—Me | H | H | H | 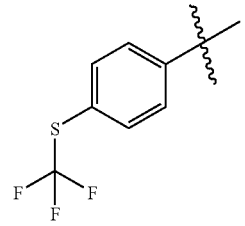 |
| 248 | OMe | H | Et | C—Me | H | H | H | 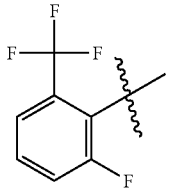 |

TABLE 1-continued
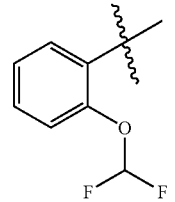
| Example number | R1 | R2 | R3 | X | R5 | R6 | R7 | R8 |
|---|---|---|---|---|---|---|---|---|
| 249 | OMe | H | Et | C—Me | H | H | H | 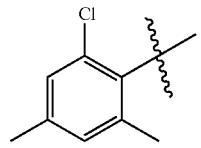 |
| 250 | OMe | H | Et | C—Me | H | H | H | 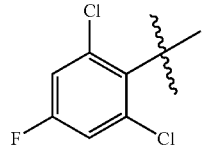 |
| 251 | OMe | H | Et | C—Me | H | H | H | 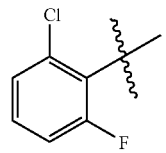 |
| 252 | OMe | H | Et | C—Me | H | H | H | 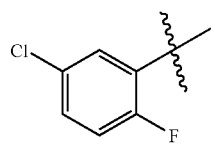 |
| 253 | OMe | H | Et | C—Me | H | H | H | 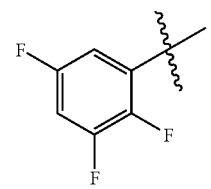 |
| 254 | OMe | H | Et | C—Me | H | H | H | 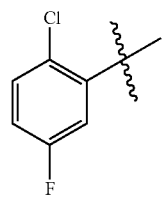 |
| 255 | OMe | H | Et | C—Me | H | H | H |  |

TABLE 1-continued

| Example number | R1 | R2 | R3 | X | R5 | R6 | R7 | R8 |
|---|---|---|---|---|---|---|---|---|
| 256 | OMe | H | Et | C—Me | H | H | H | 2,4,5-trifluorophenyl |
| 257 | OMe | H | Et | C—Me | H | H | H | 3-chloro-2-fluorophenyl |
| 258 | OMe | H | Et | C—Me | H | H | H | 4-cyano-2-fluorophenyl |
| 259 | OMe | H | Et | C—Me | H | H | H | 3-chloro-2,5-difluorophenyl |
| 260 | OEt | H | Et | CH | Cl | H | H | 2-chloro-4-fluorophenyl |
| 261 | OEt | H | Et | CH | Cl | H | H | 3-chloro-2,5-difluorophenyl |

TABLE 1-continued

| Example number | R1 | R2 | R3 | X | R5 | R6 | R7 | R8 |
|---|---|---|---|---|---|---|---|---|
| 262 | OH | H | Et | CH | Cl | H | H | 2-Cl-4-F-phenyl |
| 263 | OH | H | Et | CH | F | H | H | 2-Cl-4-F-phenyl |
| 264 | OH | H | Et | CH | OMe | H | H | 2-Cl-4-F-phenyl |
| 265 | OH | H | Et | CH | Cl | H | H | 3-Cl-2,5-diF-phenyl |
| 266 | OH | H | -CH₂CH₂N(Et)₂ | CH | H | H | H | 2-Me-4-F-phenyl |
| 267 | OH | H | Et | C—Me | H | H | H | 3-CF₃-4-F-phenyl |

TABLE 1-continued
| Example number | R1 | R2 | R3 | X | R5 | R6 | R7 | R8 |
|---|---|---|---|---|---|---|---|---|
| 268 | OH | H | Et | C—Me | H | H | H | 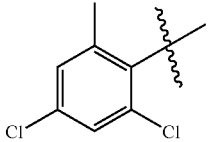 |
| 269 | OH | H | Et | C—Me | H | H | H | 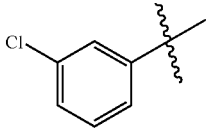 |
| 270 | OH | H | Et | C—Me | H | H | H | 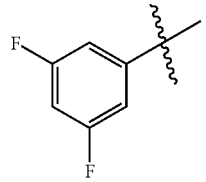 |
| 271 | OH | H | Et | C—Me | H | H | H | 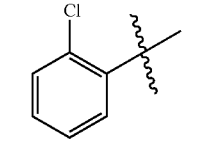 |
| 272 | OH | H | Et | C—Me | H | H | H | 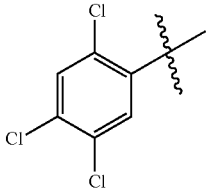 |
| 273 | OH | H | Et | C—Me | H | H | H | 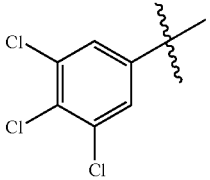 |
| 274 | OH | H | Et | C—Me | H | H | H | 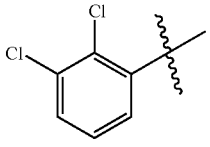 |

TABLE 1-continued
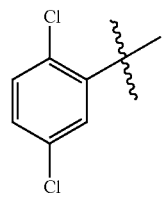
| Example number | R1 | R2 | R3 | X | R5 | R6 | R7 | R8 |
|---|---|---|---|---|---|---|---|---|
| 275 | OH | H | Et | C—Me | H | H | H | 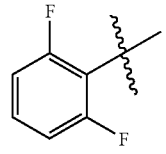 |
| 276 | OH | H | Et | C—Me | H | H | H | 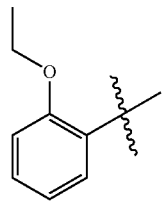 |
| 277 | OH | H | Et | C—Me | H | H | H | 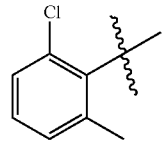 |
| 278 | OH | H | Et | C—Me | H | H | H | 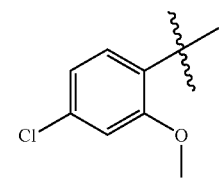 |
| 279 | OH | H | Et | C—Me | H | H | H | 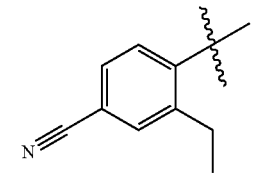 |
| 280 | OH | H | Et | C—Me | H | H | H | 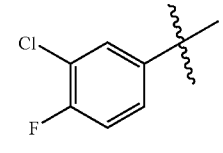 |
| 281 | OH | H | Et | C—Me | H | H | H |  |

TABLE 1-continued
| Example number | R1 | R2 | R3 | X | R5 | R6 | R7 | R8 |
|---|---|---|---|---|---|---|---|---|
| 282 | OH | H | Et | C—Me | H | H | H | 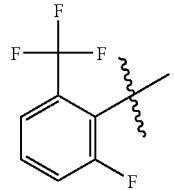 |
| 283 | OH | H | Et | C—Me | H | H | H | 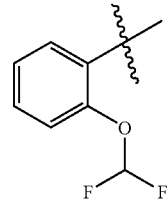 |
| 284 | OH | H | Et | C—Me | H | H | H | 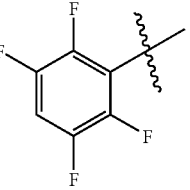 |
| 285 | OH | H | Et | C—Me | H | H | H | 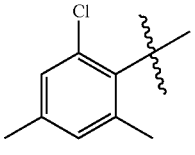 |
| 286 | OH | H | Et | C—Me | H | H | H | 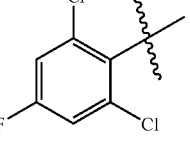 |
| 287 | OH | H | Et | C—Me | H | H | H | 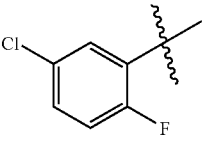 |
| 288 | OH | H | Et | C—Me | H | H | H | 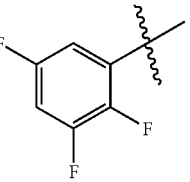 |

TABLE 1-continued
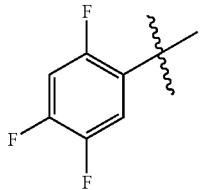
| Example number | R1 | R2 | R3 | X | R5 | R6 | R7 | R8 |
|---|---|---|---|---|---|---|---|---|
| 289 | OH | H | Et | C—Me | H | H | H | 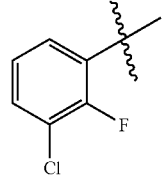 |
| 290 | OH | H | Et | C—Me | H | H | H | 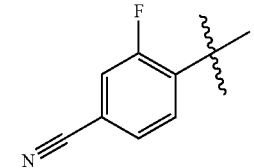 |
| 291 | OH | H | Et | C—Me | H | H | H | 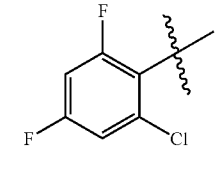 |
| 292 | OH | H | Et | C—Me | H | H | H | 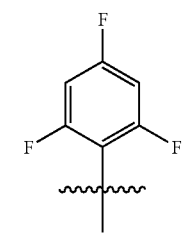 |
| 293 | OH | H | Et | CH | Cl | H | H | 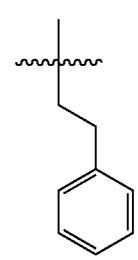 |
| 294 | OEt | H | 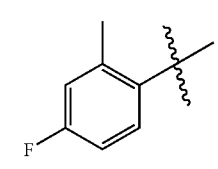 | CH | H | H | H | (2-Me, 4-F phenyl) |

TABLE 1-continued

| Example number | R1 | R2 | R3 | X | R5 | R6 | R7 | R8 |
|---|---|---|---|---|---|---|---|---|
| 295 | OEt | H | ethyl 4-(2-...oxy)ethoxy)benzoate linker | CH | Cl | H | H | 4-fluoro-2-methylphenyl |
| 296 | OEt | H | ethyl 4-(2-...oxy)ethoxy)benzoate linker | CH | Cl | H | H | 2-chloro-4-fluorophenyl |
| 297 | OEt | H | ethyl 4-(2-...oxy)ethoxy)benzoate linker | CH | Cl | H | H | 4-chloro-2-methylphenyl |

TABLE 1-continued
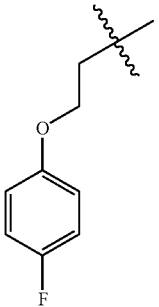
| Example number | R1 | R2 | R3 | X | R5 | R6 | R7 | R8 |
|---|---|---|---|---|---|---|---|---|
| 298 | OEt | H | 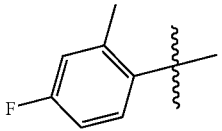 | CH | Cl | H | H | 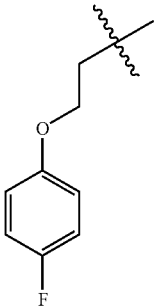 |
| 299 | OEt | H | 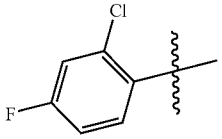 | CH | Cl | H | H | 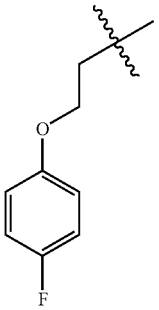 |
| 300 | OEt | H | 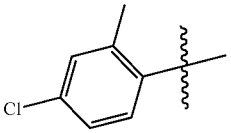 | CH | Cl | H | H | 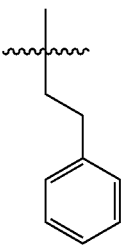 |
| 301 | OH | H | 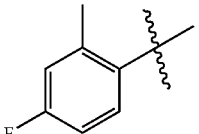 | CH | H | H | H | (see above) |

TABLE 1-continued
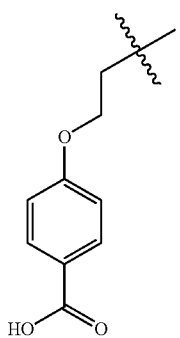
| Example number | R1 | R2 | R3 | X | R5 | R6 | R7 | R8 |
|---|---|---|---|---|---|---|---|---|
| 302 | OH | H | 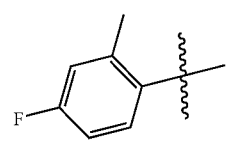 | CH | Cl | H | H | 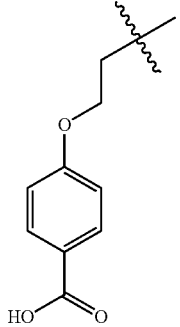 |
| 303 | OH | H | 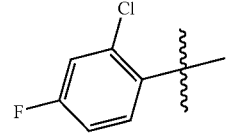 | CH | Cl | H | H | 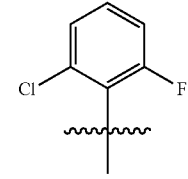 |
| 304 | OEt | H | Et | CH | H | H | H | 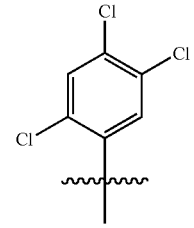 |
| 305 | OEt | H | Et | CH | H | H | H | 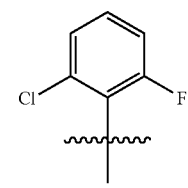 |
| 306 | OH | H | Et | CH | H | H | H | 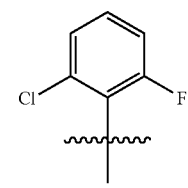 |

TABLE 1-continued

| Example number | R1 | R2 | R3 | X | R5 | R6 | R7 | R8 |
|---|---|---|---|---|---|---|---|---|
| 307 | OH | H | Et | CH | H | H | H | 2-chlorophenyl |
| 308 | OEt | H | Et | CH | H | Me | H | 2-chloro-4-fluorophenyl |
| 309 | OEt | H | Et | CH | H | Me | H | 4-fluoro-2-methylphenyl |
| 310 | OEt | H | 3-(pyrrolidin-1-yl)propyl | CH | H | H | H | 4-fluoro-2-methylphenyl |
| 311 | OH | H | Et | CH | H | H | H | 2,4,5-trichlorophenyl |

TABLE 1-continued
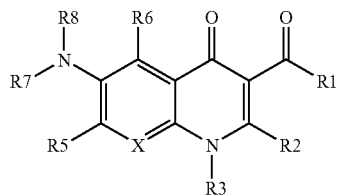
| Example number | R1 | R2 | R3 | X | R5 | R6 | R7 | R8 |
|---|---|---|---|---|---|---|---|---|
| 312 | OEt | H | methyl 2-substituted benzoate | CH | H | H | H | 2-chloro-4-fluorophenyl |
| 313 | OEt | H | methyl 3-substituted benzoate | CH | H | H | H | 2-chloro-4-fluorophenyl |
| 314 | OEt | H | methyl 4-substituted benzoate | CH | H | H | H | 2-chloro-4-fluorophenyl |
| 315 | OH | H | Et | CH | H | Me | H | 4-fluoro-2-methylphenyl |
| 316 | OH | H | 2-(pyrrolidin-1-yl)ethyl | CH | H | H | H | 4-fluoro-2-methylphenyl |

TABLE 1-continued

| Example number | R1 | R2 | R3 | X | R5 | R6 | R7 | R8 |
|---|---|---|---|---|---|---|---|---|
| 317 | OH | H | 3-carboxyphenyl | CH | H | H | H | 2-chloro-4-fluorophenyl |
| 318 | OH | H | 4-carboxyphenyl | CH | H | H | H | 2-chloro-4-fluorophenyl |
| 319 | OH | H | 2-carboxyphenyl | CH | H | H | H | 2-chloro-4-fluorophenyl |
| 320 | OEt | H | 2-(ethoxycarbonyl)phenyl | CH | Cl | H | H | 2-chloro-3,5-difluorophenyl |
| 321 | OEt | H | 4-(dimethylamino)phenyl | CH | H | H | H | 2-chloro-4-fluorophenyl |

TABLE 1-continued
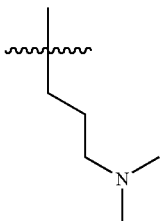
| Example number | R1 | R2 | R3 | X | R5 | R6 | R7 | R8 |
|---|---|---|---|---|---|---|---|---|
| 322 | OH | H | 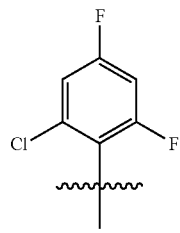 | CH | Cl | H | H | 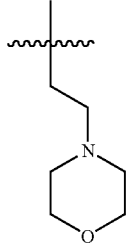 |
| 323 | OH | H | 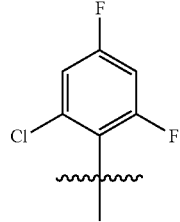 | CH | Cl | H | H | 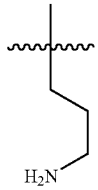 |
| 324 | OH | H | 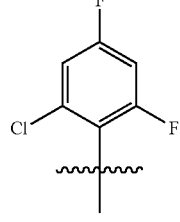 | CH | Cl | H | H | 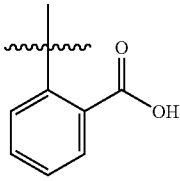 |
| 325 | OH | H | 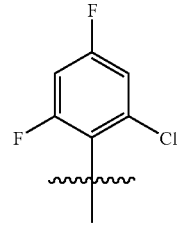 | CH | Cl | H | H | 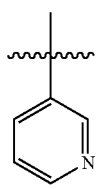 |
| 326 | OEt | H | 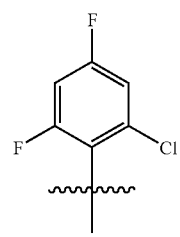 | CH | Cl | H | H |  |

TABLE 1-continued
| Example number | R1 | R2 | R3 | X | R5 | R6 | R7 | R8 |
|---|---|---|---|---|---|---|---|---|
| 327 | OH | H | 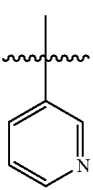 | CH | Cl | H | H | 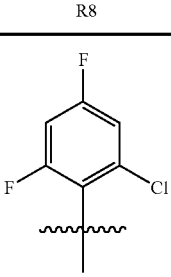 |
| 328 | OH | H | 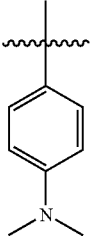 | CH | H | H | H | 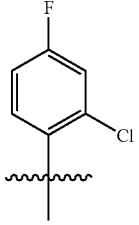 |
| 329 | OEt | H | 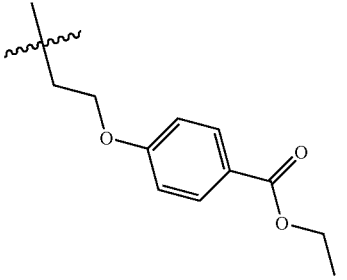 | CH | Cl | H | H | 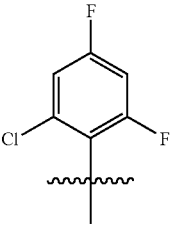 |
| 330 | OEt | H | Et | CH | H | H | H | 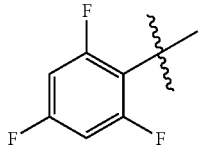 |
| 331 | OEt | H | Et | CH | H | H | H | 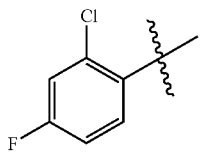 |
| 332 | OEt | H | Et | CH | H | H | H | 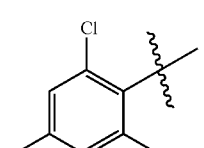 |

TABLE 1-continued

| Example number | R1 | R2 | R3 | X | R5 | R6 | R7 | R8 |
|---|---|---|---|---|---|---|---|---|
| 333 | OH | H | (CH2CH2-O-C6H4-COOH) | CH | Cl | H | H | 3-Cl-2,5-F-phenyl |
| 334 | OH | H | Et | CH | H | H | H | 2-Cl-4,6-F-phenyl |
| 335 | OH | H | Et | CH | H | H | H | 2-Cl-4-F-phenyl |
| 336 | OH | H | Et | CH | H | H | H | 2,4,6-F-phenyl |
| 337 | OEt | H | Et | CH | F | H | H | 3-Cl-2,5-F-phenyl |
| 338 | OH | H | Et | CH | F | H | H | 3-Cl-2,5-F-phenyl |

TABLE 1-continued
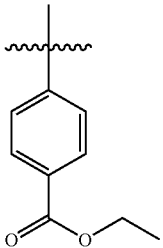
| Example number | R1 | R2 | R3 | X | R5 | R6 | R7 | R8 |
|---|---|---|---|---|---|---|---|---|
| 339 | OEt | H | 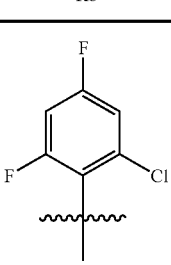 | CH | Cl | H | H | 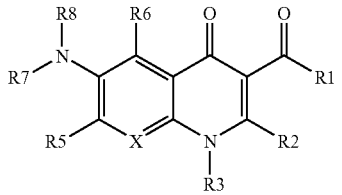 |
| 340 | OEt | H | 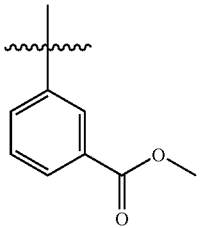 | CH | Cl | H | H | 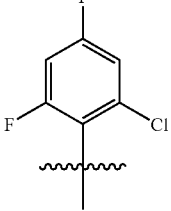 |
| 341 | OH | H | 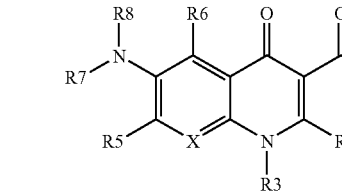 | CH | Cl | H | H | 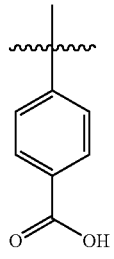 |
| 342 | OH | H | 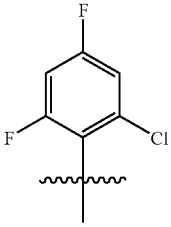 | CH | Cl | H | H | 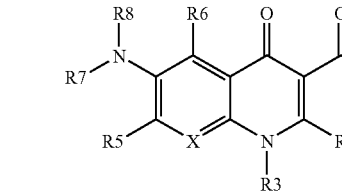 |
| 343 | OEt | H | 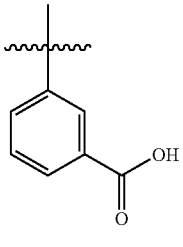 | CH | H | H | H | 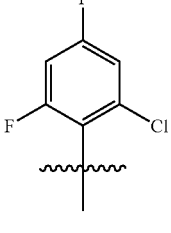 |

TABLE 1-continued

| Example number | R1 | R2 | R3 | X | R5 | R6 | R7 | R8 |
|---|---|---|---|---|---|---|---|---|
| 344 | OEt | H | pentanoic acid chain | CH | Cl | H | H | 2-chloro-3,5-difluorophenyl |
| 345 | OEt | H | 2-phenylethyl | CH | Cl | H | H | 2-chloro-3,5-difluorophenyl |
| 346 | OH | H | 2-phenylethyl | CH | Cl | H | H | 2-chloro-3,5-difluorophenyl |
| 347 | OH | H | pentanoic acid chain | CH | Cl | H | H | 2-chloro-3,5-difluorophenyl |
| 348 | OH | H | 3-(1H-pyrazol-1-yl)propyl | CH | Cl | H | H | 2-chloro-3,5-difluorophenyl |

TABLE 1-continued

| Example number | R1 | R2 | R3 | X | R5 | R6 | R7 | R8 |
|---|---|---|---|---|---|---|---|---|
| 349 | OH | H | -CH2-(2-pyridyl) | CH | Cl | H | H | 3-Cl-2,5-F2-phenyl |
| 350 | OH | H | -CH2-(4-pyridyl) | CH | Cl | H | H | 3-Cl-2,5-F2-phenyl |
| 351 | OH | H | -CH2-(3-pyridyl) | CH | Cl | H | H | 3-Cl-2,5-F2-phenyl |
| 352 | OH | H | 3-pyridyl | CH | Cl | H | H | 3-Cl-2,5-F2-phenyl |
| 353 | OH | H | -CH2-COOH | CH | Cl | H | H | 3-Cl-2,5-F2-phenyl |

TABLE 1-continued

| Example number | R1 | R2 | R3 | X | R5 | R6 | R7 | R8 |
|---|---|---|---|---|---|---|---|---|
| 354 | OH | H | (CH2-CH2-COOH) | CH | Cl | H | H | 2-Cl-3,5-diF-phenyl |
| 355 | OEt | H | (CH2-C6H4-COOMe) | CH | Cl | H | H | 2-Cl-3,5-diF-phenyl |
| 356 | OH | H | (CH2-C6H4-COOH) | CH | Cl | H | H | 2-Cl-3,5-diF-phenyl |
| 357 | OH | H | (2-methylphenyl) | CH | Cl | H | H | 2-Cl-3,5-diF-phenyl |
| 358 | OEt | H | (CH2CH2CH2-morpholino) | CH | Cl | H | H | 2-Cl-3,5-diF-phenyl |

TABLE 1-continued

| Example number | R1 | R2 | R3 | X | R5 | R6 | R7 | R8 |
|---|---|---|---|---|---|---|---|---|
| 359 | OH | H | 2-fluorophenyl | CH | Cl | H | H | 3-chloro-2,5-difluorophenyl |
| 360 | OH | H | 3-morpholinopropyl | CH | Cl | H | H | 2-chloro-4,6-difluorophenyl |
| 361 | OH | H | 3-morpholinopropyl | CH | Cl | H | H | 2-chloro-4,6-difluorophenyl |
| 362 | OEt | H | (pyridin-4-yl)methyl | CH | Cl | H | H | 3-chloro-2,5-difluorophenyl |
| 363 | OEt | H | 2-carboxyethyl | CH | Cl | H | H | 3-chloro-2,5-difluorophenyl |

TABLE 1-continued

| Example number | R1 | R2 | R3 | X | R5 | R6 | R7 | R8 |
|---|---|---|---|---|---|---|---|---|
| 364 | OEt | H | CH2-(3-pyridyl) | CH | Cl | H | H | 2,6-difluoro-3-chlorophenyl (3,5-difluoro-4-...) |

The activity of the compounds was assayed as follows:

Glycogen Phosphorylase a Activity Assay

The effect of compounds on the activity of the active form of glycogen phosphorylase (GPa) was measured in the reverse direction by following the synthesis of glycogen from glucose 1-phosphate by determining the liberation of inorganic phosphate. All the reactions were carried out as duplicate determinations in microtiter plates with 96 wells (Half Area Plates, Costar No 3696), measuring the change in absorption owing to the formation of the reaction product at the wavelength specified hereinafter in a Multiskan Ascent Elisa Reader (Lab Systems, Finland).

In order to measure the GPa enzymic activity in the reverse direction, the general method of Engers et al. (Engers H D, Shechosky S, Madsen N B, Can J Biochem 1970 July; 48(7): 746-754) was used to measure the conversion of glucose 1-phosphate into glycogen and inorganic phosphate, with the following modifications: human glycogen phosphorylase a (for example with 0.76 mg of protein/ml (Aventis Pharma Deutschland GmbH), dissolved in buffer solution E (25 mM β-glycerophosphate, pH 7.0, 1 mM EDTA and 1 mM dithiothreitol) was diluted with buffer T (50 mM Hepes, pH 7.0, 100 mM KCl, 2.5 mM EDTA, 2.5 mM $MgCl_2 \cdot 6H_2O$) and addition of 5 mg/ml glycogen to a concentration of 10 µg of protein/ml. Test substances were prepared as 10 mM solution in DMSO and diluted to 50 µM with buffer solution T. To 10 µl of this solution were added 10 µl of 37.5 mM glucose, dissolved in buffer solution T, and 5 mg/mL glycogen, plus 10 µl of a solution of human glycogen phosphorylase a (10 µg of protein/ml) and 20 µl of glucose 1-phosphate, 2.5 mM. The baseline glycogen phosphorylase a activity in the absence of test substance was determined by adding 10 µl of buffer solution T (0.1% DMSO). The mixture was incubated at room temperature for 40 minutes, and the liberated inorganic phosphate was measured by the general method of Drueckes et al. (Drueckes P, Schinzel R, Palm D, *Anal Biochem* 1995 September 1;230(1):173-177) with the following modifications: 50 µl of a stop solution of 7.3 mM ammonium molybdate, 10.9 mM zinc acetate, 3.6% ascorbic acid, 0.9% SDS are added to 50 µl of the enzyme mixture. After incubation at 45° C. for 60 minutes, the absorption at 820 nm was measured. To determine the background absorption, in a separate mixture the stop solution was added immediately after addition of the glucose 1-phosphate solution.

This test was carried out with a concentration of 10 µM of the test substance in order to determine the particular inhibition of glycogen phosphorylase a in vitro by the test substance.

TABLE 2

Biological activity

| Ex. | % inhibition at 10 µM |
|---|---|
| 1 | 14 |
| 4 | 30 |
| 6 | 82 |
| 10 | 54 |
| 14 | 13 |
| 31 | 51 |
| 33 | 77 |
| 35 | 16 |
| 47 | 71 |
| 51 | 12 |
| 57 | 91 |
| 58 | 97 |
| 68 | 56 |
| 71 | 29 |
| 79 | 31 |
| 87 | 24 |
| 92 | 96 |
| 94 | 103 |
| 98 | 83 |
| 100 | 89 |
| 104 | 64 |
| 106 | 96 |
| 109 | 89 |
| 110 | 10 |
| 114 | 14 |
| 120 | 34 |
| 122 | 95 |
| 126 | 26 |
| 127 | 34 |
| 142 | 23 |
| 143 | 3 |
| 144 | 18 |
| 150 | 21 |
| 156 | 8 |
| 180 | 4 |

TABLE 2-continued

Biological activity

| Ex. | % inhibition at 10 μM |
|---|---|
| 181 | 55 |
| 182 | 4 |
| 191 | 13 |
| 196 | 20 |
| 200 | 69 |
| 204 | 6 |
| 212 | 84 |
| 219 | 100 |
| 221 | 100 |
| 232 | 88 |
| 236 | 65 |
| 264 | 102 |
| 267 | 3 |
| 280 | 33 |
| 282 | 41 |
| 283 | 23 |
| 284 | 10 |
| 290 | 97 |
| 294 | 96 |
| 300 | 97 |
| 302 | 55 |
| 309 | 11 |
| 310 | 54 |
| 320 | 68 |
| 322 | 95 |
| 323 | 99 |
| 324 | 95 |
| 325 | 98 |
| 326 | 95 |
| 328 | 74 |
| 329 | 54 |

It is evident from the table that the compounds of the formula I inhibit the activity of glycogen phosphorylase a and are thus very suitable for lowering the blood glucose level.

The preparation of some examples is described in detail below, and the other compounds of the Formula I were obtained analogously:

Experimental Part:

EXAMPLE 1

1-Ethyl-6-(4-ethylphenylamino)-7-methyl-4-oxo-1, 4-dihydro-[1,8]naphthyridine-3-carboxylate (Variant A of the Palladium-Catalyzed Amination)

100 mg of ethyl 6-bromo-1-ethyl-7-methyl-4-oxo-1,4-dihydro-[1,8]naphthyridine-3-carboxylate were transferred together with 37 mg of 4-ethylaniline, 20 mg of Pd(OAc)$_2$, 60 mg of BINAP and 250 mg of cesium carbonate into a suitable reaction vessel, a protective gas atmosphere was generated with argon, and 10 ml of dioxane were added. The mixture was then heated at 80° C. for 8 h.

The pure product was isolated from the reaction solution by chromatography on an HPLC system. This entailed use of a Merck Purospher RP-18 column and an acetonitrile:water mixture as eluent; the initial acetonitrile content was 15% and rose to 95% over the course of 20 minutes.

Yield: 45%

EXAMPLE 167

Methyl 1-ethyl-6-(4-methoxy-2-methylphenylamino)-8-methyl-4-oxo-1,4-dihydroquinolone-3-carboxylate (Variant B of the Palladium-Catalyzed Amination)

100 mg of methyl 6-bromo-1-ethyl-8-methyl-4-oxo-1,4-dihydroquinolone-3-carboxylate were transferred together with 42.3 mg of 4-methoxy-2-methylaniline, 20 mg of Pd(OAc)2, 60 mg of XANTPHOS and 250 mg of cesium carbonate into a suitable reaction vessel, a protective gas atmosphere was generated with argon, and 10 ml of dioxane were added. The mixture was then heated at 80° C. for 8 h.

The pure product was isolated from the reaction solution by chromatography on an HPLC system. This entailed use of a Merck Purospher RP-18 column and an acetonitrile:water mixture as eluent; the initial acetonitrile content was 15% and rose to 100% over the course of 20 minutes.

Yield: 40%

EXAMPLE 199

1-Ethyl-6-(4-methoxy-2-methylphenylamino)-8-methyl-4-oxo-1,4-dihydroquinolone-3-carboxylic acid Methyl 1-ethyl-6-(4-methoxy-2-methylphenylamino)-8-methyl-4-oxo-1,4-dihydroquinolone-3-carboxylate (30 mg) was dissolved in 5 ml of dioxane, 2.5 equivalents of a 1 N NaOH solution were added, and the mixture was heated at 60° C. for 4 h. Removal of the solvent in vacuo was followed by chromatography on an HPLC system to purify the product. This entailed use of a Merck Purospher-RP18 column and an acetonitrile:water mixture as eluent; the initial acetonitrile content was 15% and rose to 95% over the course of 20 minutes.

Yield: 75%

All other ester cleavages were carried out in an analogous way.

Preparation of the Intermediate IXa

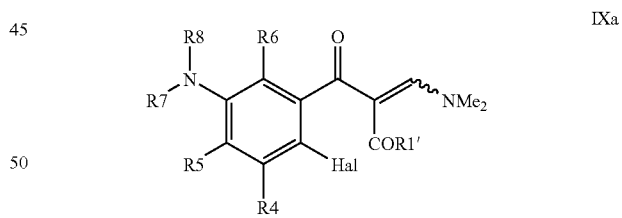

IXa

Variant A:

a) Ethyl 2,4-dichloro-5-(2-chloro-4,6-difluorophenylamino) benzoate

A solution of 100 mg (0.34 mmol) of ethyl 5-bromo-2,4-dichlorobenzoate, 197 mg (0.6 mmol) of cesium carbonate, 70 mg (0.12 mmol) of Xantphos, 23 mg (0.10 mmol) of palladium acetate and 60 mg (0.37 mmol) of 6-chloro-2,4-difluoroaniline in 3 ml of dimethoxyethane was heated at 100° C. for 2 hours. After cooling to room temperature, the mixture was filtered with suction through kieselguhr and chromatographed on silica gel (heptane:ethyl acetate=99:1 to 90:10 in 90 minutes). 70 mg (55%) of the product were obtained.

b) 2,4-Dichloro-5-(2-chloro-4,6-difluorophenylamino)benzoic acid 120 mg (0.31 mmol) of ethyl 2,4-dichloro-5-(2-chloro-4,6-difluorophenylamino)benzoate were suspended in 6 ml of an ethanol/2 N sodium hydroxide solution mixture (1:1) and heated at 90° C. for 3 hours. After cooling to room temperature, the pH was adjusted to 2 with 2 N sulfuric acid, and the precipitate was filtered off with suction. 98 mg (88%) of the product were obtained.

c) Ethyl 2-[2,4-dichloro-5-(2-chloro-4,6-difluorophenylamino)benzoyl]-3-dimethylaminoacrylate 95 mg (0.27 mmol) of 2,4-dichloro-5-(2-chloro-4,6-difluorophenylamino)benzoic acid were boiled with 0.98 ml of thionyl chloride under reflux for 3 hours. The thionyl chloride was distilled off, and the residue was mixed with 3 ml of toluene and concentrated in vacuo. The residue was taken up in 2 ml of toluene and added to a solution of 39 mg (0.27 mmol) of ethyl 3-dimethylaminoacrylate, 6 μl of triethylamine and 1 ml of toluene. The mixture was heated at 90° C. for 3 hours. The mixture was concentrated and chromatographed on silica gel (heptane:ethyl acetate=75:25 to 0:100 in 45 minutes). 30 mg (23%) of the desired product were obtained.

MS: M+H=477/479

This intermediate was employed for example for the synthesis of example 327.

Variant B:

a) Ethyl 3-[2,4-dichloro-5-(2-chloro-4,6-difluorophenylamino)phenyl]-3-oxopropionate 3.0 g (8.51 mmol) of 2,4-dichloro-5-(2-chloro-4,6-difluorophenylamino)benzoic acid (variant A b)) and 9.3 ml of thionyl chloride were heated at 70° C. for 1.5 hours. The mixture was diluted with 20 ml of dry toluene and concentrated. The residue was twice mixed with toluene and again evaporated.

1.4 ml of a 1.6 M solution of butyllithium in hexane was added to a solution of 3.47 g (17.0 mmol) of ethyl trimethylsilyl malonate in 45 ml of diethyl ether at −75° C. in such a way that the temperature did not rise above −60° C. The mixture was then stirred at −75° C. for 30 minutes. The 2,4-dichloro-5-(2-chloro-4,6-difluorophenylamino)benzoyl chloride was dissolved in 45 ml of dimethoxyethane and added dropwise in 40 minutes. The mixture was slowly warmed to 10° C. and stirred at this temperature for 2.5 hours. The reaction mixture was diluted with ethyl acetate and washed twice each with 250 ml portions of water and saturated sodium bicarbonate solution. The organic phase was dried and concentrated. 3.88 g of the crude mixture were obtained and were reacted without further purification in the next stage.

b) Ethyl 2-[2,4-dichloro-5-(2-chloro-4,6-difluorophenylamino)benzoyl]-3-dimethylaminoacrylate A solution of 3.88 g (crude) of ethyl 3-[2,4-dichloro-5-(2-chloro-4,6-difluorophenylamino)phenyl]-3-oxopropionate and 1.22 g (0.10 mmol) of dimethylformamide dimethyl acetal in 10 ml of toluene were heated to reflux for 1.5 hours. The mixture was cooled to room temperature and concentrated in vacuo. Purification on silica gel (petroleum ether) (45-70° C.)/ethyl acetate, 8 minutes isocratic 35% ethyl acetate, then to 60% ethyl acetate in 7 minutes, flow rate 400 ml/minute) afforded 3.59 g (82% over the two stages) of the desired product.

MS: M+H=477/479

EXAMPLE 327

7-Chloro-6-(2-chloro-4,6-difluorophenylamino)-4-oxo-1-pyridin-3-yl-1,4-dihydroquinolone-3-carboxylic acid a) Ethyl 2-[2,4-dichloro-5-(2-chloro-4,6-difluorophenylamino)benzoyl]-3-(pyridin-3-yl-amino)acrylate A solution of 30 mg (0.06 mmol) of ethyl 2-[2,4-dichloro-5-(2-chloro-4,6-difluorophenylamino) benzoyl]-3-dimethylaminoacrylate and 15 mg (0.16 mmol) of 3-aminopyridine in 2 ml of toluene were heated at 150° C. for 7 hours. Concentration resulted in 33 mg of the desired product, which were employed without further purification in the next stage.

b) Ethyl 7-chloro-6-(2-chloro-4,6-difluorophenylamino)-4-oxo-1-pyridin-3-yl-1,4-dihydro quinolone-3-carboxylate A suspension of 33 mg (0.06 mmol) of ethyl 2-[2,4-dichloro-5-(2-chloro-4,6-difluorophenyl amino)benzoyl]-3-(pyridin-3-ylamino)acrylate, 10 mg (0.08 mmol) of potassium carbonate and 1 ml of dimethylformamide were heated at 90° C. for 5 hours. The mixture was concentrated and purified by reversed phase HPLC (Purospher RP-18, acetonitrile/water). 12 mg (37%) of the desired product were obtained.

c) 7-Chloro-6-(2-chloro-4,6-difluorophenylamino)-4-oxo-1-pyridin-3-yl-1,4-dihydro quinolone-3-carboxylic acid 12 mg (0.02 mmol) of ethyl 7-chloro-6-(2-chloro-4,6-difluorophenylamino)-4-oxo-1-pyridin-3-yl-1,4-dihydroquinolone-3-carboxylate were suspended in 6 ml of an ethanol/2 N sodium hydroxide solution mixture (1:1) and heated at 90° C. for 3 hours. After cooling to room temperature, the pH was adjusted to 2 with 2 N hydrochloric acid and the precipitate was filtered off with suction. 6 mg (53%) of the product were obtained.

MS: M+H=462/464

The invention claimed is:

1. A compound of the formula I

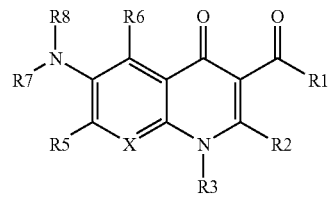

in which the meanings are

R1 is OH, O—($C_1$-$C_6$)-alkyl or O—($C_1$-$C_6$)-alkyl-OCO—($C_1$-$C_6$)-alkyl;

R2 is H, ($C_1$-$C_6$)-alkyl or phenyl;

R3 is H, ($C_1$-$C_8$)-alkyl, ($C_3$-$C_7$)-cycloalkyl, pyridyl or phenyl, wherein ($C_1$-$C_8$)-alkyl and ($C_3$-$C_7$)-cycloalkyl may be substituted by R9 and wherein said phenyl and pyridyl may be substituted by R10;

R9 is $NH_2$, NH—($C_1$-$C_6$)-alkyl, N—(($C_1$-$C_6$)-alkyl)$_2$, COOH, COO—($C_1$-$C_6$)-alkyl, ($C_3$-$C_7$)-cycloalkyl, heteroalkyl, heteroaryl, O-phenyl or phenyl, wherein said heteroaryl, O-phenyl and phenyl may be substituted by R11;

R10 is F, Cl, Br, ($C_1$-$C_6$-alkyl), O—($C_1$-$C_6$)-alkyl, COOH, COO—($C_1$-$C_6$)-alkyl, $NH_2$, NH—($C_1$-$C_6$)-alkyl or N—(($C_1$-$C_6$)-alkyl)$_2$;

R11 is F, Cl, ($C_1$-$C_6$-alkyl), O—($C_1$-$C_6$)-alkyl, $NH_2$, NH—($C_1$-$C_6$)-alkyl, N—(($C_1$-$C_6$)-alkyl)$_2$, COOH or COO—($C_1$-$C_4$)-alkyl;

X is C—R4 or N;

R4 is H, F, Cl, Br, OH, $NO_2$, CN, ($C_1$-$C_6$)-alkyl or O—($C_1$-$C_6$)-alkyl, wherein said ($C_1$-$C_6$)-alkyl and O—($C_1$-$C_6$)-alkyl may be substituted more than once by F, Cl or Br;

R5 is H, F, Cl, Br, OH, $NO_2$, CN, ($C_1$-$C_6$)-alkyl or O—($C_1$-$C_6$)-alkyl, where said ($C_1$-$C_6$)-alkyl and O—($C_1$-$C_6$)-alkyl may be substituted more than once by F, Cl or Br;

R6 is H, F, Cl, Br, $NO_2$, CN or ($C_1$-$C_6$)-alkyl, wherein said ($C_1$-$C_6$)-alkyl may be substituted more than once by F, Cl or Br;

R7 is H or ($C_1$-$C_6$)-alkyl;

R8 is phenyl, wherein said phenyl may be substituted up to five times by F, Cl, Br, CN, $NO_2$, ($C_1$-$C_8$)-alkyl, O—($C_1$-$C_8$)-alkyl, S—($C_1$-$C_8$)-alkyl, ($C_2$-$C_8$)-alkenyl, ($C_3$-$C_7$)-cycloalkyl, CO—($C_1$-$C_4$)-alkyl, phenyl, benzyl, benzoyl, $NH_2$, NH—($C_1$-$C_6$)-alkyl, N—(($C_1$-$C_6$)-alkyl)$_2$, P(O)—(O—($C_1$-$C_4$)-alkyl)$_2$ or heteroalkyl, wherein said ($C_1$-$C_8$)-alkyl, O—($C_1$-$C_8$)-alkyl, S—($C_1$-$C_8$)-alkyl, ($C_2$-$C_8$)-alkenyl, ($C_3$-$C_7$)-cycloalkyl, CO—($C_1$-$C_4$)-alkyl, NH—($C_1$-$C_6$)-alkyl, N—(($C_1$-$C_6$)-alkyl)$_2$, P(O)—(O—($C_1$-$C_4$)-alkyl)$_2$ and heteroalkyl may be substituted more than once by F, Cl, Br, COOH, or COO—($C_1$-$C_4$)-alkyl;

heteroalkyl is heterocyclic, saturated or unsaturated 4- to 7-membered ring which may comprise up to 3 heteroatoms N, O or S as ring members, wherein said ring may be substituted by F, Cl, Br, CN, $NO_2$, ($C_1$-$C_4$)-alkyl, OH, COOH or COO—($C_1$-$C_4$)-alkyl;

with the exception of compounds of the formula I in which the radicals simultaneously have the following meaning:

X equal to N, R1 equal to OH, R2, R3, R4, R5 and R7 equal to H and R8 equal to unsubstituted phenyl;

and the physiologically tolerated salts thereof.

2. The compound of claim 1 wherein

R1 is OH, O—($C_1$-$C_6$)-alkyl or O—($C_1$-$C_6$)-alkyl-OCO—($C_1$-$C_6$)-alkyl;

R2 is H, ($C_1$-$C_6$)-alkyl or phenyl;

R3 is ($C_1$-$C_8$)-alkyl, ($C_3$-$C_7$)-cycloalkyl, pyridyl or phenyl, wherein said ($C_1$-$C_8$)-alkyl and ($C_3$-$C_7$)-cycloalkyl may be substituted by R9 and wherein said phenyl and pyridyl may be substituted by R10;

R9 is $NH_2$, NH—($C_1$-$C_6$)-alkyl, N—(($C_1$-$C_6$)-alkyl)$_2$, COOH, COO—($C_1$-$C_6$)-alkyl, ($C_3$-$C_7$)-cycloalkyl, heteroalkyl, heteroaryl, O-phenyl or phenyl, wherein said heteroaryl, O-phenyl and phenyl may be substituted by R11;

R10 is F, Cl, Br, ($C_1$-$C_6$-alkyl), O—($C_1$-$C_6$)-alkyl, COOH, COO—($C_1$-$C_6$)-alkyl, $NH_2$, NH—($C_1$-$C_6$)-alkyl or N—(($C_1$-$C_6$)-alkyl)$_2$;

R11 is F, Cl, ($C_1$-$C_6$-alkyl), O—($C_1$-$C_6$)-alkyl, $NH_2$, NH—($C_1$-$C_6$)-alkyl, N—(($C_1$-$C_6$)-alkyl)$_2$, COOH or COO—($C_1$-$C_4$)-alkyl;

X is C—R4 or N;

R4 is H, F, Cl, Br, OH, $NO_2$, CN, ($C_1$-$C_6$)-alkyl or O—($C_1$-$C_6$)-alkyl, wherein said ($C_1$-$C_6$)-alkyl and O—($C_1$-$C_6$)-alkyl may be substituted more than once by F, Cl or Br;

R5 is H, F, Cl, Br, OH, $NO_2$, CN, ($C_1$-$C_6$)-alkyl or O—($C_1$-$C_6$)-alkyl, where said ($C_1$-$C_6$)-alkyl and O—($C_1$-$C_6$)-alkyl may be substituted more than once by F, Cl or Br;

R6 is H, F, Cl, Br, $NO_2$, CN or ($C_1$-$C_6$)-alkyl, wherein said ($C_1$-$C_6$)-alkyl may be substituted more than once by F, Cl or Br;

R7 is H or ($C_1$-$C_6$)-alkyl;

R8 is phenyl, wherein said phenyl may be substituted up to five times by F, Cl, Br, CN, $NO_2$, ($C_1$-$C_8$)-alkyl, O—($C_1$-$C_8$)-alkyl, S—($C_1$-$C_8$)-alkyl, ($C_2$-$C_8$)-alkenyl, ($C_3$-$C_7$)-cycloalkyl, CO—($C_1$-$C_4$)-alkyl, phenyl, benzyl, benzoyl, $NH_2$, NH—($C_1$-$C_6$)-alkyl, N—(($C_1$-$C_6$)-alkyl)$_2$, P(O)—(O—($C_1$-$C_4$)-alkyl)$_2$ or heteroalkyl, wherein said ($C_1$-$C_8$)-alkyl, O—($C_1$-$C_8$)-alkyl, S—($C_1$-$C_8$)-alkyl, ($C_2$-$C_8$)-alkenyl, ($C_3$-$C_7$)-cycloalkyl, CO—($C_1$-$C_4$)-alkyl, NH—($C_1$-$C_6$)-alkyl, N—(($C_1$-$C_6$)-alkyl)$_2$, P(O)—(O—($C_1$-$C_4$)-alkyl)$_2$ and heteroalkyl may be substituted more than once by F, Cl, Br, COOH, or COO—($C_1$-$C_4$)-alkyl;

heteroalkyl is heterocyclic, saturated or unsaturated 4- to 7-membered ring which may comprise up to 3 heteroatoms N, O or S as ring members, where said ring may be substituted by F, Cl, Br, CN, $NO_2$, ($C_1$-$C_4$)-alkyl, OH, COOH or COO—($C_1$-$C_4$)-alkyl.

3. The compound of claim 1 wherein

R1 is OH, O—($C_1$-$C_6$)-alkyl or O—($C_1$-$C_6$)-alkyl-OCO—($C_1$-$C_6$)-alkyl;

R2 is H;

R3 is phenyl, wherein said phenyl may be substituted by R10;

R10 is F, Cl, Br, ($C_1$-$C_6$-alkyl), O—($C_1$-$C_6$)-alkyl, COOH, COO—($C_1$-$C_6$)-alkyl, $NH_2$, NH—($C_1$-$C_6$)-alkyl or N—(($C_1$-$C_6$)-alkyl)$_2$;

X is C—R4;

R4 is H or ($C_1$-$C_6$)-alkyl;

R5 is H, F, Cl or ($C_1$-$C_6$)-alkyl;

R6 is H;

R7 is H;

R8 is phenyl, wherein said phenyl may be substituted up to five times by F, Cl;

and the physiologically tolerated salts thereof.

4. The compound of claim 1 wherein

R1 is OH, O—($C_1$-$C_6$)-alkyl;

R2 is H;

R3 is phenyl, wherein said phenyl is substituted by R10;

R10 is COOH or COO—($C_1$-$C_6$)-alkyl;

X is C—R4;

R4 is H or ($C_1$-$C_6$)-alkyl;

R5 is F, Cl or ($C_1$-$C_6$)-alkyl;

R6 is H;

R7 is H;

R8 is phenyl, wherein said phenyl is substituted one to five times by F, Cl;

and the physiologically tolerated salts thereof.

5. A pharmaceutical composition comprising one or more compounds of claim 1 and a pharmaceutically acceptable carrier.

* * * * *